(12) United States Patent
Sahatjian et al.

(10) Patent No.: US 7,976,936 B2
(45) Date of Patent: Jul. 12, 2011

(54) ENDOPROSTHESES

(75) Inventors: Ronald A. Sahatjian, Lexington, MA (US); Francisca Tan, Boston, MA (US); Patrick T. Mather, Chagrin Falls, OH (US); Changdeng Liu, Storrs, CT (US); Qing Ge, Coventry, CT (US)

(73) Assignees: University of Connecticut, Storrs, CT (US); Boston Scientific SciMed, Inc., Maple Grove, MN (US)

( * ) Notice: Subject to any disclaimer, the term of this patent is extended or adjusted under 35 U.S.C. 154(b) by 1510 days.

(21) Appl. No.: 11/111,509

(22) Filed: Apr. 21, 2005

(65) Prior Publication Data
US 2005/0251249 A1 Nov. 10, 2005

Related U.S. Application Data

(63) Continuation-in-part of application No. 10/958,435, filed on Oct. 5, 2004, now Pat. No. 7,794,494, which is a continuation-in-part of application No. 10/683,314, filed on Oct. 10, 2003, now abandoned.

(60) Provisional application No. 60/488,323, filed on Jul. 18, 2003, provisional application No. 60/488,590, filed on Jul. 18, 2003.

(51) Int. Cl.
*B32B 3/00* (2006.01)

(52) U.S. Cl. ......................................................... 428/210

(58) Field of Classification Search .................. 428/195, 428/209, 210; 427/34, 12, 503, 504, 510, 427/515; 424/422; 425/199, 222; 623/1.42, 623/1.46
See application file for complete search history.

(56) References Cited

U.S. PATENT DOCUMENTS

| | | | |
|---|---|---|---|
| 3,383,336 A | 5/1968 | Kuyama et al. |
| 3,459,725 A | 8/1969 | Natta et al. |
| 3,563,973 A | 2/1971 | Arditti et al. |
| 4,080,357 A | 3/1978 | Gergen et al. |
| 4,503,569 A | 3/1985 | Dotter |
| 4,531,933 A | 7/1985 | Norton et al. |
| 4,612,241 A | 9/1986 | Howard, Jr. |
| 4,893,623 A | 1/1990 | Rosenbluth |
| 4,969,890 A | 11/1990 | Sugita et al. |
| 4,990,155 A | 2/1991 | Wilkoff |
| 5,007,926 A | 4/1991 | Derbyshire |
| 5,037,427 A | 8/1991 | Harada et al. |
| 5,062,829 A | 11/1991 | Pryor et al. |
| 5,064,435 A | 11/1991 | Porter |
| 5,089,005 A | 2/1992 | Harada |
| 5,100,429 A | 3/1992 | Sinofsky et al. |
| 5,145,935 A | 9/1992 | Hayashi |
| 5,147,385 A | 9/1992 | Beck et al. |
| 5,163,952 A | 11/1992 | Froix |

(Continued)

FOREIGN PATENT DOCUMENTS

DE 102 28 120 A1 1/2004

(Continued)

OTHER PUBLICATIONS

Liu et al., "Themomechanical Characterization of a Novel Series of Shape Memory Polymers", SPE ANTEC Proceedings, 5 pages, 2002.

(Continued)

*Primary Examiner* — Kevin T Truong
(74) *Attorney, Agent, or Firm* — Fish & Richardson P.C.

(57) ABSTRACT

Endoprostheses are disclosed.

26 Claims, 15 Drawing Sheets

U.S. PATENT DOCUMENTS

| | | | |
|---|---|---|---|
| 5,189,110 A | 2/1993 | Ikematu et al. | |
| 5,258,020 A | 11/1993 | Froix | |
| 5,278,237 A | 1/1994 | Kita | |
| 5,282,854 A | 2/1994 | Yagi et al. | |
| 5,395,882 A | 3/1995 | Siol et al. | |
| 5,421,955 A | 6/1995 | Lau et al. | |
| 5,461,114 A | 10/1995 | Kita | |
| 5,466,242 A | 11/1995 | Mori | |
| 5,496,311 A | 3/1996 | Abele et al. | |
| 5,506,300 A | 4/1996 | Ward et al. | |
| 5,607,467 A | 3/1997 | Froix | |
| 5,645,559 A | 7/1997 | Hachtman et al. | |
| 5,665,822 A | 9/1997 | Bitler et al. | |
| 5,674,241 A | 10/1997 | Bley et al. | |
| 5,674,242 A | 10/1997 | Phan et al. | |
| 5,741,333 A | 4/1998 | Frid | |
| 5,755,769 A | 5/1998 | Richard et al. | |
| 5,769,883 A | 6/1998 | Buscemi et al. | |
| 5,776,162 A | 7/1998 | Kleshinski | |
| 5,800,516 A | 9/1998 | Fine et al. | |
| 5,830,179 A | 11/1998 | Mikus et al. | |
| 5,849,037 A | 12/1998 | Frid | |
| 5,876,432 A | 3/1999 | Lau et al. | |
| 5,880,240 A | 3/1999 | Tsuno | |
| 5,889,118 A | 3/1999 | Delgado et al. | |
| 5,900,246 A | 5/1999 | Lambert | |
| 5,900,444 A | 5/1999 | Zamore | |
| 5,908,918 A | 6/1999 | Chen et al. | |
| 5,910,357 A | 6/1999 | Hachisuka et al. | |
| 5,928,217 A | 7/1999 | Mikus et al. | |
| 5,935,506 A | 8/1999 | Schmitz et al. | |
| 5,954,744 A | 9/1999 | Phan et al. | |
| 5,955,559 A | 9/1999 | Handlin, Jr. et al. | |
| 5,961,547 A | 10/1999 | Razavi | |
| 5,964,744 A | 10/1999 | Balbierz et al. | |
| 5,968,070 A | 10/1999 | Bley et al. | |
| 5,997,563 A | 12/1999 | Kretzers | |
| 6,024,764 A | 2/2000 | Schroeppel | |
| 6,033,413 A | 3/2000 | Mikus et al. | |
| 6,086,204 A | 7/2000 | Magnante | |
| 6,086,610 A | 7/2000 | Duerig et al. | |
| 6,139,536 A | 10/2000 | Mikus et al. | |
| 6,156,842 A | 12/2000 | Hoenig et al. | |
| 6,160,084 A | 12/2000 | Langer et al. | |
| 6,174,305 B1 | 1/2001 | Mikus et al. | |
| 6,179,878 B1 | 1/2001 | Duerig et al. | |
| 6,183,248 B1 | 2/2001 | Chishti et al. | |
| 6,217,609 B1 | 4/2001 | Haverkost | |
| 6,241,691 B1 | 6/2001 | Ferrera et al. | |
| 6,248,129 B1 | 6/2001 | Froix | |
| 6,283,992 B1 | 9/2001 | Hankh et al. | |
| 6,287,326 B1 | 9/2001 | Pecor | |
| 6,315,791 B1 | 11/2001 | Gingras et al. | |
| 6,323,459 B1 | 11/2001 | Maynard | |
| 6,348,065 B1 | 2/2002 | Brown et al. | |
| 6,364,904 B1 | 4/2002 | Smith | |
| 6,368,346 B1 | 4/2002 | Jadhav | |
| 6,388,043 B1 | 5/2002 | Langer et al. | |
| 6,390,812 B1 | 5/2002 | Chishti et al. | |
| 6,395,038 B1 | 5/2002 | Schroeppel | |
| 6,413,273 B1 | 7/2002 | Baum et al. | |
| 6,416,545 B1 | 7/2002 | Mikus et al. | |
| 6,478,773 B1 | 11/2002 | Gandhi et al. | |
| 6,485,298 B2 | 11/2002 | Chishti et al. | |
| 6,485,507 B1 | 11/2002 | Walak et al. | |
| 6,517,569 B2 | 2/2003 | Mikus et al. | |
| 6,517,570 B1 | 2/2003 | Lau et al. | |
| 6,530,950 B1 | 3/2003 | Alvarado et al. | |
| 6,538,089 B1 | 3/2003 | Samra et al. | |
| 6,596,818 B1 | 7/2003 | Zamore | |
| 6,641,899 B1* | 11/2003 | Colburn et al. | 428/209 |
| 6,679,605 B2 | 1/2004 | Zhou et al. | |
| 6,705,861 B2 | 3/2004 | Chishti et al. | |
| 6,720,402 B2 | 4/2004 | Langer et al. | |
| 6,852,825 B2 | 2/2005 | Lendlein et al. | |
| 6,858,680 B2 | 2/2005 | Gunatillake et al. | |
| 7,067,606 B2 | 6/2006 | Mather et al. | 528/37 |
| 7,091,297 B2 | 8/2006 | Mather et al. | 528/28 |
| 7,198,639 B2 | 4/2007 | Lai et al. | 623/6.11 |
| 2001/0029398 A1 | 10/2001 | Jadhav | |
| 2002/0007222 A1 | 1/2002 | Desai | |
| 2002/0015519 A1 | 2/2002 | Tokas et al. | |
| 2002/0055787 A1 | 5/2002 | Lennox et al. | |
| 2002/0137864 A1 | 9/2002 | Tong | |
| 2002/0151967 A1 | 10/2002 | Mikus et al. | |
| 2002/0156523 A1 | 10/2002 | Lau et al. | |
| 2002/0198584 A1 | 12/2002 | Unsworth et al. | |
| 2003/0040803 A1 | 2/2003 | Rioux et al. | |
| 2003/0060530 A1 | 3/2003 | Topolkaraev et al. | |
| 2003/0060793 A1 | 3/2003 | Topolkaraev et al. | |
| 2003/0147046 A1 | 8/2003 | Shadduck | |
| 2003/0191276 A1 | 10/2003 | Lendlein et al. | |
| 2004/0014929 A1 | 1/2004 | Lendlein et al. | |
| 2004/0015187 A1 | 1/2004 | Lendlein et al. | |
| 2004/0015261 A1 | 1/2004 | Hofmann et al. | |
| 2004/0024098 A1 | 2/2004 | Mather et al. | |
| 2004/0024143 A1 | 2/2004 | Lendlein et al. | |
| 2004/0030062 A1 | 2/2004 | Mather et al. | |
| 2004/0116641 A1 | 6/2004 | Mather et al. | |
| 2004/0122174 A1 | 6/2004 | Mather et al. | |
| 2004/0122184 A1 | 6/2004 | Mather et al. | |
| 2005/0010012 A1* | 1/2005 | Jost et al. | 528/34 |
| 2005/0010275 A1 | 1/2005 | Sahatjian et al. | |
| 2005/0216074 A1 | 9/2005 | Sahatjian et al. | |
| 2005/0245719 A1 | 11/2005 | Mather et al. | |
| 2006/0041089 A1 | 2/2006 | Mather et al. | |

FOREIGN PATENT DOCUMENTS

| | | |
|---|---|---|
| EP | 0 183 272 A2 | 6/1986 |
| EP | 0 183 372 A1 | 6/1986 |
| EP | 0 277 816 A1 | 8/1988 |
| EP | 0 343 442 | 5/1989 |
| EP | 0 324 946 A2 | 7/1989 |
| EP | 0 343 442 A2 | 11/1989 |
| EP | 0 368 274 | 11/1989 |
| EP | 0 385 443 | 2/1990 |
| EP | 0 368 274 A2 | 5/1990 |
| EP | 0 385 443 A2 | 9/1990 |
| EP | 0 404 004 A2 | 12/1990 |
| EP | 0 422 693 | 2/1991 |
| EP | 0 422 693 B1 | 6/1995 |
| EP | 1 000 958 | 11/1998 |
| EP | 1 00 958 A1 | 5/2000 |
| EP | 1 016 424 A1 | 7/2000 |
| JP | 612301051 | 10/1986 |
| JP | 62192440 | 8/1987 |
| JP | 63145325 | 6/1988 |
| JP | 63145325 A | 6/1988 |
| JP | 63179955 | 7/1988 |
| JP | 2274526 | 8/1990 |
| JP | 2232212 | 9/1990 |
| JP | 02-258845 | 10/1990 |
| JP | 2255830 | 10/1990 |
| JP | 2255830 A | 10/1990 |
| JP | 2258817 | 10/1990 |
| JP | 3068610 | 3/1991 |
| JP | 3068611 | 3/1991 |
| JP | 04-109133 | 4/1992 |
| JP | 4100831 | 4/1992 |
| JP | 07-292040 | 11/1995 |
| JP | 8301952 | 11/1996 |
| JP | 9235329 | 9/1997 |
| JP | 1997309986 A | 12/1997 |
| JP | 10-001545 | 1/1998 |
| JP | 11-154420 | 8/1999 |
| JP | 11302493 | 11/1999 |
| JP | 2000119465 A | 4/2000 |
| JP | 2000319423 | 11/2000 |
| JP | 2005102953 | 4/2005 |
| WO | WO 94/14890 | 7/1994 |
| WO | WO 95/26762 | 10/1995 |
| WO | WO 97/46633 | 12/1997 |
| WO | WO 99/42147 | 8/1999 |
| WO | WO 99/42528 | 8/1999 |
| WO | WO 99/42548 | 8/1999 |
| WO | WO 99/46327 | 9/1999 |
| WO | WO 00/10485 | 3/2000 |

| | | |
|---|---|---|
| WO | WO 00/15840 | 3/2000 |
| WO | WO 00/32131 | 6/2000 |
| WO | WO 00/33770 | 6/2000 |
| WO | WO0032131 A1 | 6/2000 |
| WO | WO 00/46262 | 8/2000 |
| WO | WO 00/71554 | 11/2000 |
| WO | WO 00/71554 A2 | 11/2000 |
| WO | WO 00/78246 A2 | 12/2000 |
| WO | WO 01/07499 | 2/2001 |
| WO | WO 01/07499 A1 | 2/2001 |
| WO | WO 01/10871 | 2/2001 |
| WO | WO 01/56641 | 8/2001 |
| WO | WO 01/91822 | 12/2001 |
| WO | WO 01/91822 A1 | 12/2001 |
| WO | WO 02/19591 A2 | 2/2002 |
| WO | WO 02/39875 | 5/2002 |
| WO | WO 02/39875 A2 | 5/2002 |
| WO | WO 02/059170 | 8/2002 |
| WO | WO 2002/060498 | 8/2002 |
| WO | WO 02/083786 | 10/2002 |
| WO | WO 02/083786 A1 | 10/2002 |
| WO | WO 01/80936 A1 | 11/2002 |
| WO | WO 01/93783 A2 | 12/2002 |
| WO | WO 03/015840 A3 | 2/2003 |
| WO | WO 03/035743 | 5/2003 |
| WO | WO 03/035743 A1 | 5/2003 |
| WO | WO 03/084490 | 10/2003 |
| WO | WO 03/084490 A1 | 10/2003 |
| WO | WO 03/084491 | 10/2003 |
| WO | WO 03/084491 A1 | 10/2003 |
| WO | WO 03/088818 | 10/2003 |
| WO | WO 03/088818 A2 | 10/2003 |
| WO | WO 03/093341 | 11/2003 |
| WO | WO 2004/006885 | 1/2004 |
| WO | WO 2004/006885 A2 | 1/2004 |
| WO | WO 2004/011525 | 2/2004 |
| WO | WO 2004/032799 | 4/2004 |
| WO | WO 2004/032799 A2 | 4/2004 |
| WO | WO 2004/033515 | 4/2004 |
| WO | WO 2004/033515 A2 | 4/2004 |
| WO | WO 2004/033539 | 4/2004 |
| WO | WO 2004/033539 A1 | 4/2004 |
| WO | WO 2004/033553 | 4/2004 |
| WO | WO 2004/033553 A1 | 4/2004 |
| WO | WO 2004/073690 A1 | 9/2004 |
| WO | WO 2004/090042 A1 | 10/2004 |
| WO | WO 2004/110515 A1 | 12/2004 |
| WO | WO 2005/009523 | 2/2005 |
| WO | WO 2005/070988 A1 | 8/2005 |
| WO | WO 2006/115799 A1 | 11/2006 |

OTHER PUBLICATIONS

Gordon, "Applications of Shape Memory Polyurethanes", Proceedings of the First International Conference on Shape Memory and Superelastic Technologies, SMST International Committee, pp. 115-199, 1994.
Yoshida et al., "Development and Application of Shape-Memory Polymer Gel (Part 1)-Synthesis and Processing of Shape-Memory Polymer Gel", Hokkaidoritsu Kogyo Shikenjo Hokoku, 298 Abstract Only, 1 page, 1999.
Ishii, "Shape Memory Resins", Trans-polyisoprene-based Shape Memory Resins, Zairyo Gijutsu, 7(6), Abstract only, 1 page, 1989.
JP 02255830 Abstract Only; Oct. 16, 1990 (1 page).
JP 02274526 Abstract Only; Nov. 8, 1990 (1 page).
JP 11154420 Abstract Only; Jun. 8, 1999 (1 page).
JP 11302493 Abstract Only; Nov. 2, 1999 (1 page).
JP 2232212 Abstract Only; Sep. 14, 1990 (1 page).
JP 2258817 Abstract Only; Oct. 19, 1990 (1 page).
JP 3068610 Abstract Only; Mar. 25, 1991 (1 page).
JP 3068611 Abstract Only; Mar. 25, 1991 (1 page).
JP 4100831 Abstract Only; Apr. 2, 1992 (1 page).
JP 62192440 Abstract Only; Aug. 24, 1987 (1 page).
JP 61231051 Abstract Only; Oct. 15, 1986 (1 page).
JP 63145325 Abstract Only; Jun. 17, 1988 (1 page).
JP 63179955 Abstract Only; Jul. 23, 1988 (1 page).
JP 8301952 Abstract Only; Nov. 19, 1996 (1 page).
JP 9235329 Abstract Only; Sep. 9, 1997 (1 page).
JP 2000319423 Abstract Only; Nov. 21, 2000 (1 page).
Liu, et al., "Chemically Cross-Linked Polycylooctene: Synthesis, Characterization and Shape Memory Behavior" Macromolecules, (2002), 35, pp. 9868-9874.
Dinger, et al., "High Turnover Numbers with Ruthenium-Based Metathesis Catalysts" Advanced Synthesis Catalysis, vol. 344 (2002) pp. 671-677.
Oh et al., "Dynamic Mechanical Properties of Carbon Black Filled Trans-polyoctenamer Vulcanizates" (Oct. 19, 1985) Abstract Only, 1 page.
Lendlein et al., Biodegradable, Elastic Shape-Memory Polymers for Potential Biomedical Applications, Science (2002) 296, pp. 1673-1676.
Nakayama, K., "Properties and Applications of Shape-Memory Polymers", International Polymer Science and Technology 1991, 18, T/43-48.
Irie, M., Shape Memory Polymers, Cambridge University Press: Cambridge, UK 1998, pp. 203-219.
Boochathum et al., 'Vulcanizaton of Cis- and Trans-Polyisoprene and Their Blends: Crystallization Characteristics and Properties, European Polymer Journal, 37 (2001) pp. 429-434.
Boochathum et al., "Vulcanization of Cis- and Trans-Polyisoprene and Their Blends: Cure Characteristics and Crosslink Distribution", European Polymer Journal 37 (2001) pp. 417-427.
Schwab et al., "Synthesis and Applications of $RuCl_2(=CHR')(PR_3)_2$: The Influence of the Alkylidene Moiety on Metathesis Activity", J. Am. Chem. Soc. (1996) 118, pp. 100-110.
Bielawski et al., "Highly Efficient Ring-Opening Metathesis Polymerization (ROMP) Using New Ruthenium Catalysts Containing N-Heterocyclic Carbene Ligands", Angew. Chem. Int. Ed. (2000) 39, No. 16, pp. 2903-2906.
Calderon et al., "Melting Temperature of trans-Polyoctenamer", Journal of Polymer Science: Part A-2, vol. 5, (1967), pp. 1283-1292.
Natta et al., "The Monoclinic Structure of Even trans-Polyalkenamers", European Polymer Journal, vol. 3 (1967) pp. 339-352.
Bassi et al., "The Triclinic Structure of trans-Polyoctenamer", European Polymer Journal, vol. 4, (1968), pp. 123-132.
Schneider et al., "Crystallinity of trans-Polyoctenamer: Characterization and Influence of Sample History", Journal of Molecular Catalysis, 46 (1988), pp. 395-403.
Yeh et al., "Radiation-Induced Crosslinking: Effect on Structure of Polyethylene", Colloid & Polymer Sci. 263 (1985), pp. 109-115.
Fu et al., "Nanoscale Reinforcement of Polyhedral Oligomeric Silsesquioxane (POSS) in Polyurethane Elastomer", Polymer Int. 49 (2000) pp. 437-440.
Qing Ge and Patrick T. Mather, "Synthesis of Thermoplastic Polyurethanes Bearing Nanostructured Hard Segments: New Shape Memory Polymers" Polymer Program, Institute of Materials Science and Department of Engineering, UCONN, (Jul. 2003), (Abstract, 2 pages).
Fu et al., "Structural Development During Deformation of Polyurethane Containing Polyhedral Oligomeric Silsesquioxanes (POSS) Molecules", Polymer 42 (2001) pp. 599-611.
Du Prez, F. E. et al., "Segmented Networks by Cationic Polymerization: Design and Applications" NATO Sci. Ser., Ser. E, (1999), pp. 75-98.
Goethals et al. "Poly(Vinyl Ethers) as Building Blocks for New Materials" Macromol. Symp., (1998), 132, pp. 57-64.
Kagami et al., "Shape Memory Behaviors of Crosslinked Copolymers Containing Stearyl Acrylate" Macromol. Rapid. Commun., (1996), 17(8), pp. 539-543.
Kaneko et al., "Shape Memory Gels with Multi-Stimuli-Responses", Proc. SPIE-Int. Soc. Opt. Eng., (1999) 3669, pp. 199-208.
Reyntjens et al., "Polymer Networks Containing Crystallizable Poly(octadecyl vinyl ether) Segments for Shape-Memory Materials", Macromol. Rapid. Commun., (1999), 20(5), pp. 251-255.
H. G. Jeon et al., "Shape Memory and Nanostructure in Poly(norbornyl-POSS) Copolymers", Polymer International, 49, (2000), pp. 453-457.
P. T. Mather et al., "Strain Recovery in Drawn POSS Hybrid Thermoplastics," XIIIth International Congress on Rheology, Cambridge, UK (2000), 4, pp. 53-55.

P. T. Mather et al., "Strain Recovery in POSS Hybrid Thermoplastics," Polymer Preprints 41(1), (2000), pp. 528-529.

Lendlein et al., "AB-Polymer Networks Based on Oligo(ε-caprolactone) Segments Showing Shape-Memory Properties" Proc. Natl. Acad. Sci., USA (2001), 98(3), pp. 842-847.

Wei et al., "Shape-Memory Materials and Hybrid Composites for Smart Systems", Journal of Materials Science 33, (1998) pp. 3743-3762.

Van Humbeeck, "Shape Memory Alloys: A Material and a Technology", Advanced Engineering Materials, vol. 3, No. 11, (2001) pp. 837-850.

Byung Kyu Kim et al, "Polyurethane Ionomers Having Shape Memory Effects", Polymer, vol. 39, No. 13 (1998), pp. 2803-2808.

Lin et al., "Study on Shape-Memory Behavior of Polyether-Based Polyurethanes. I. Influence of the Hard-Segment Content", Journal of Applied Polymer Science, vol. 69, (1998), pp. 1563-1574.

Lin et al., "Study on Shape-Memory Behavior of Polyether-Based Polyurethanes. II. Influence of Soft-Segment Molecular Weight", Journal of Applied Polymer Science, vol. 69, (1998), pp. 1575-1586.

Chun et al., "Enhanced Dynamic Mechanical and Shape-Memory Properties of a Poly(ethylene terephthalate)-Poly(ethylene glycol) Copolymer Crosslinked by Maleic Anhydride", Journal of Applied Polymer Science, vol. 83, (2002) pp. 27-37.

Gajria et al., "Miscibility and Biodegradability of Blends of Poly(Lactic Acid) and Poly(Vinyl Acetate)", Polymer, vol. 37, (1996), pp. 437-444.

Ishii, M. "Shape Memory Resins", Trans-polyisoprene-based Shape Memory Resins, Zairyo Gijutsu (1989), 7(6), Abstract Only, 1 page.

Lendlein, Andreas and Steffen Kelch, "Shape-Memory Polymers", Angew. Chem. Int. Ed. 41, (2002), pp. 2034-2057.

Ingrid A. Rousseau and Patrick T. Mather, "Shape Memory Effect Exhibited by Smectic-C Liquid Crystalline Elastomers" J. Am. Chem. Soc., 125, (2003), pp. 15300-15301.

Liu et al., "Shape Memory of Hydrogen-Bonded Polymer Network/ Poly(ethylene glycol) Complexes", Chengdu Institute of Organic Chemistry, Chinese Academy of Sciences, Dec. 30, 2003 (5 pages).

Jeong et al., "Miscibility and Shape Memory Property of Poly(vinyl chloride)/Thermoplastic Polyurethane Blends", Journal of Materials Science 36 (2001) 5457-5463.

Jeong et al., "Miscibility and Shape Memory Effect of Thermoplastic Polyurethane Blends with Phenoxy Resin", European Polymer Journal 37 (2001) 2245-2252.

Zhu, G. et al., "Shape-Memory Effects of Radiation Crosslinked Poly(ε-caprolactone)", Journal of Applied Polymer Science, vol. 90, 1589-1595 (2003).

Yoshida et al., "Development and Application of Shape-Memory Polymer Gel (Part I)-Synthesis and Processing of Shape-Memory Polymer Gel", Hokkaidoritsu Kogyo Shikenjo Hokoku (1999), 298 Abstract Only, 1 page.

"Silsesquioxanes, Bridging the Gap Between Polymers & Ceramics" ChemFiles vol. 1, No. 6 (2001) (14 pgs).

Ramanathan et al., "Polyurethane Urea", Polymer Data Handbook, New York: Oxford University Press (1999), pp. 878-881.

Ramanathan et al., "Polyurethane Elastomers", Polymer Data Handbook, New York: Oxford University Press (1999), pp. 874-877.

Ramanathan et al., "Polyurethane", Polymer Data Handbook, New York: Oxford University Press (1999), pp. 870-873.

Sung et al., "Properties of Segmented Poly(urethaneureas) Based on 2,4-Toluene Diisocyanate. 1. Thermal transitions, X-ray Studies, and Comparison with Segmented Poly(urethanes)", Macromolecures, 13, (1980), pp. 111-116.

Gupta et al., "Effect of Solvent Exposure on the Properties of Hydroxy-Terminated Polybutadiene-Based Polyurethanes", Polym Int, 52, (2003), pp. 938-948.

Bielawski et al., "Highly Efficient Syntheses of Acetoxy- and Hydroxy-Terminated Telechelic Poly(butadiene)s Using Ruthenium Catalysts Containing N-heterocyclic Ligands", Polymer, 42, (2001), pp. 4939-4945.

Sarbu et al., "Synthesis of Hydroxy-Telechelic Poly(methyl acrylate) and Polystyrene by Atom Transfer Radical Coupling", Macromolecules, 37, (2004), pp. 9694-9700.

Mauler et al., Liquid-Crystalline Polyacrylate Crosslinked with α, ω Polyisoprene Diacrylate Segments, Polymer Bulletin, 41, (1998) pp. 291-297.

Sartomer Product Bulletin, "Hydroxyl Terminated Polybutadiene Resins and Derivatives-Poly bd and Krasol" Sep. 2004, 40 pages.

Wache et al., "Development of a Polymer Stent with Shape Memory Effect as a Drug Delivery System", Journal of Materials Science: Materials in Medicine, 14, (2003), pp. 109-112.

Valimaa et al., "Viscoelastic Memory and Self-Expansion of Self-Reinforced Bioabsorbable Stents", Biomaterials, 23, (2002), pp. 3575-3582.

"Suite of Shape-Memory Polymers", Chemical & Engineering, Feb. 5, 2001, 1 page.

Woojin Lee, "Polymer Gel Based Actuator: Dynamic Model of Gel for Real Time Control", Massachusetts Institute of Technology, Department of Mechanical Engineering, May 1996, 120 pages.

Brochure, Degussa High Performance Polymers, The Rubber with Unique Properties, Vestenamer©, Undated, 12 pages.

Gordon, "Applications of Shape Memory Polyurethanes", Proceedings of the First International Conference on Shape Memory and Superelastic Technologies, SMST International Committee, (1994), pp. 115-199.

Liu et al., "Thermomechanical Characterization of a Novel Series of Shape Memory Polymers", SPE ANTEC Proceedings, (2002) 5 pages.

WO9746633 Abstract Only; Dec. 11, 1997 (1 page).

WO0046262 Abstract Only; Aug. 10, 2000 (1 page).

EP0343442 Abstract Only; Nov. 29, 1989 (1 page).

Schwab et al., "Hybrid Nanoreinforced Polyurethanes Based on Polyhedral Oligomeric Silsesquioxanes (POSS)"; Rapra Abstracts; Pergamon Press Ltd., Oxford, GB, vol. 77, No. 6, Jun. 1999 (Abstract Only) (2 pages).

Schwab et al. Hybrid Nanoreinforced Polyurethanes Based on Polyhedral Oligomeric Silsesquioxanes (POSS), Am. Chem. Soc. PMSE Prep., 1997, 77, pp. 549-550.

Sarbu et al., "Synthesis of Hydroxy-Telechelic Poly(methyl acrylate) and Polystyrene by Atom Transfer Radical Coupling", Macromolecules, 37, pp. 9694-9700, 2004.

"Hydroxyl Terminated Polybutadiene Resins and Derivatives—Poly bd® and Krasol®", Sartomer Product Bulletin, Sep. 2004.

Zhu et al., "Shape-Memory Effects of Radiation Crosslinked Poly(ε-caprolactone)", Journal of Applied Polymer Science, vol. 90, pp. 1589-1595, 2003.

Rousseau et al., "Shape Memory Effect Exhibited by Smectic-C Liquid Crystalline Elastomers" J. Am. Chem. Soc., 125, pp. 15300-15301, 2003.

Gupta et al., "Effect of solvent exposure on the Properties of hydroxy-terminated polybutadiene-based polyurethanes", Polym. Int. 52, pp. 938-948, 2003.

Liu et al., "Shape Memory of Hydrogen-Bonded Polymer Network/ Poly(ethylene glycol) Complexes", Chengdu Institute of Organic Chemistry, Chinese Academy of Sciences, 2003.

Ge et al., "Synthesis of Thermoplastic Polyurethanes Bearing Nanostructured Hard Segments: New Shape Memory Polymers" Polymer Program, Institute of Materials Science and Department of Engineering, UCONN, (Abstract, 2 pp.), Jul. 2003.

Wache et al., "Development of a polymer stent with shape memory effect as a drug delivery system", Journal of Materials Science: Materials in Medicine, 14, 109-112, (2003).

Lendlein et al., "Biodegradable, Elastic Shape-Memory Polymers for Potential Biomedical Applications", Science, vol. 296, May 31, 2002.

Liu, et al., "Chemically Cross-Linked Polycylooctene: Synthesis, Characterization and Shape Memory Behavior" Macromolecules, 35, pp. 9868-9874, 2002.

Dinger, et al., "High Turnover Numbers with Ruthenium-Based Metathesis Catalysts" Advanced Synthesis Catalysis, vol. 344, pp. 671-677, 2002.

Lendlein et al., "Shape-Memory Polymers", Angew. Chem. Int. Ed. 41, pp. 2034-2057, 2002.

Chun et al., "Enhanced Dynamic Mechanical and Shape-Memory Properties of a Poly(ethylene terephthalate)-Poly(ethylene glycol)

Copolymer Crosslinked by Maleic Anhydride", Journal of Applied Polymer Science, vol. 83, pp. 27-37, 2002.

Valimaa et al., "Viscoelastic memory and self-expansion of self-reinforced bioabsorbable stents", Biomaterials, 23, pp. 3575-3582, 2002.

"Suite of Shape-Memory Polymers", Chemical & Engineering, Feb. 5, 2001.

Jeong et al., "Miscibility and Shape Memory Effect of Thermoplastic Polyurethane Blends with Phenoxy Resin", European Polymer Journal , 37, pp. 2245-2252, 2001.

Van Humbeeck, "Shape Memory Alloys: A Material and a Technology", Advanced Engineering Materials, vol. 3, No. 11, pp. 837-850, 2001.

Fu et al., "Structural Development During Deformation of Polyurethane Containing Polyhedral Oligomeric Silsesquioxanes (POSS) Molecules", Polymer 42, pp. 599-611, 2001.

Boochathum et al., "Vulcanization of Cis- and Trans-Polyisoprene and Their Blends: Cure Characteristics and Crosslink Distribution", European Polymer Journal 37, pp. 417-427, 2001.

Boochathum et al., Vulcanization of Cis- and Trans-Polyisoprene and Their Blends: Crystallization Characteristics and Properties, European Polymer Journal, 37, pp. 429-434, 2001.

"Silsesquioxanes, Bridging the Gap Between Polymers & Ceramics" ChemFiles vol. 1, No. 6, 2001.

Bielawski et al., "Highly efficient syntheses of acetoxy- and hydroxy-terminated telechelic poly(butadiene)s using ruthenium catalysts containing N-heterocyclic ligands", Polymer, 42 , pp. 4939-4945, 2001.

Mather et al., "Strain Recovery in Drawn POSS Hybrid Thermoplastics," XIIIth International Congress on Rheology, Cambridge, UK, 4, pp. 53-55, 2000.

Mather et al., "Strain Recovery in POSS Hybrid Thermoplastics," Polymer Preprints 41(1), pp. 528-529, 2000.

Jeon et al., "Shape Memory and Nanostructure in Poly(norbornyl-POSS) Copolymers", Polymer International, 49, pp. 453-457, 2000.

Fu et al., "Nanoscale Reinforcement of Polyhedral Oligomeric Silsesquioxane (POSS) in Polyurethane Elastomer", Polymer Int. 49, pp. 437-440, 2000.

Bielawski et al., "Highly Efficient Ring-Opening Metathesis Polymerization (ROMP) Using New Ruthenium Catalysts Containing N-Heterocyclic Carbene Ligands", Angew. Chem. Int. Ed., 39, No. 16, pp. 2903-2906, 2000.

Reyntjens et al., "Polymer Networks Containing Crystallizable Poly(octadecyl vinyl ether) Segments for Shape-Memory Materials", Macromol. Rapid. Commun., 20(5), pp. 251-255, 1999.

Du Prez et al., "Segmented Networks by Cationic Polymerization: Design and Applications" NATO Sci. Ser., Ser. E, pp. 75-98, 1999.

Ramanathan et al., "Polyurethane", Polymer Data Handbook, pp. 870-873, 1999.

Ramanathan et al., "Polyurethane elastomers", Polymer Data Handbook, pp. 874-877, 1999.

Ramanathan et al., "Polyurethane urea", Polymer Data Handbook, pp. 878-881, 1999.

Kaneko et al., "Shape Memory Gels with Multi-Stimuli-Responses", Proc. SPIE-Int. Soc. Opt. Eng., 3669, pp. 199-208, 1999.

Lin et al., "Study on Shape-Memory Behavior of Polyether -Based Polyurethanes. II. Influence of Soft-Segment Molecular Weight", Journal of Applied Polymer Science, vol. 69, pp. 1575-1586, 1998.

Lin et al., "Study on Shape-Memory Behavior of Polyether-Based Polyurethanes. I. Influence of the Hard-Segment Content", Journal of Applied Polymer Science, vol. 69, pp. 1563-1574, 1998.

Kim et al., "Polyurethane Ionomers Having Shape Memory Effects", Polymer , vol. 39, No. 13, pp. 2803-2808, 1998.

Wei et al., "Shape-Memory Materials and Hybrid Composites for Smart Systems", Journal of Materials Science 33, pp. 3743-3762, 1998.

Goethals et al. "Poly(Vinyl Ethers) as Building Blocks for New Materials" Macromol. Symp., 132, pp. 57-64, 1998.

Mauler et al., "Liquid-crystalline polyacrylate crosslinked with $\alpha, \omega$ polyisoprene diacrylate segments", Polymer Bulletin, 41, pp. 291-297, 1998.

Irie, Shape Memory Polymers, Cambridge University Press: Cambridge, UK, pp. 203-219, 1998.

Paul Starck, "Dynamic Mechanical Thermal Analysis on Ziegler-Natta and Metallocene Type Ethylene Copolymers", Eur. Poly. J. vol. 33, No. 3, pp. 339-348, 1997.

Woojin Lee, "Polymer Gel Based Actuator: Dynamic model of gel for real time control", Massachusetts Institute of Technology, Department of Mechanical Engineering, May 3, 1996.

Gajria et al., "Miscibility and Biodegradability of Blends of Poly(Lactic Acid) and Poly(Vinyl Acetate)", Polymer, vol. 37, pp. 437-444, 1996.

Mauler et al., "Functional Group Determination in Hydroxilated Polymer", Eur. Polym. J., vol. 31, No. 1, pp. 51-55, 1995.

Sung et al., "Properties of Segmented Poly(urethaneureas) Based on 2,4-Toluene Diisocyanate. 1. Thermal Transitions, X-ray Studies, and Comparison with Segmented Poly(urethanes)", Macromolecules, 13, pp. 111-116, 1980.

Kagami et al., "Shape Memory Behaviors of Crosslinked Copolymers Containing Stearyl Acrylate" Macromol. Rapid. Commun., 17(8), pp. 539-543, 1996.

Schwab et al., "Synthesis and Applications of RuC12(=CHR')(PR3)2: The Influence of the Alkylidene Moiety on Metathesis Activity", J. Am. Chem. Soc., 118, pp. 100-110, 1996.

Nakayama, K., "Properties and Applications of Shape-Memory Polymers", International Polymer Science and Technology, 18, T/43-48, 1991.

Schneider et al., "Crystallinity of trans-Polyoctenamer: Characterization and Influence of Sample History", Journal of Molecular Catalysis, 46, pp. 395-403, 1988.

Yeh et al., "Radiation-Induced Crosslinking: Effect on Structure of Polyethylene", Colloid & Polymer Sci. 263, pp. 109-115, 1985.

Oh et al., "Dynamic Mechanical Properties of Carbon Black Filled Trans-polyoctenamer Vulcanizates", Abstract Only, (Oct. 19, 1985).

Bassi et al., "The Triclinic Structure of trans-Polyoctenamer", European Polymer Journal, vol. 4, pp. 123-132, 1968.

Natta et al., "The Monoclinic Structure of Even Trans-Polyalkenamers", European Polymer Journal, vol. 3, pp. 339-352, 1967.

Calderon et al., "Melting Temperature of trans-Polyoctenamer", Journal of Polymer Science: Part A-2, vol. 5, pp. 1283-1292, 1967.

Brochure, Degussa High Performance Polymers, The Rubber with Unique Properties, Vestenamer©, Undated.

Kannan et al., "Polyhedral Oligomeric Silsesquixoane Nanocomposites: The Next Generation Material for Biomedical Applications", Acc. Chem. Res., vol. 38, No. 11, pp. 879-884, 2005.

Fu et al., "Structural Development during deformation of polyurethane containing polyhedral oligomeric silsesquioxanes (POSS) molecules", Polymer, 42, pp. 599-611, 2001.

Fan et al., "Synthesis and Properties of Polyurethane Modified with Aminoethylaminopropyl Poly(dimethyl siloxane)", Journal of Applied Polymer Science, vol. 74, pp. 2552-2558, 1999.

Schwabb et al., "Polyhedral Oligomeric Sil silsesquioxanes (POSS): Silicon Based Monomers and Their Use in the Preparation of Hybrid Polyurethanes", Mat. Res. Soc. Symp. Proc., vol. 519, pp. 21-27, 1998.

Schwab et al., "Hybrid Nanoreinforced Polyurethanes Based on Polyhedral Oligomeric Silsesquioxanes(Poss)", ACS Polymeric Materials Science and Engineering, Fall Meeting, 1997, vol. 77, pp. 549-550.

* cited by examiner

R = isobutyl $n\,RSi(OH)_3 \xrightarrow{-x\,H_2O} [RSiO_{3/2}]_n(H_2O)_{3n/2-x} \xrightarrow{-(3n/2-x)\,H_2O} [RSiO_{3/2}]_n$ 1           2           3

ENDOPROSTHESES

CROSS REFERENCE TO RELATED APPLICATIONS

This application is a continuation-in-part of U.S. patent application Ser. No. 10/958,435, filed Oct. 5, 2004, now U.S. Pat. No. 7,794,494; which is a continuation-in-part of U.S. patent application Ser. No. 10/683,314, filed Oct. 10, 2003, now abandoned; which claims the benefit of priority from U.S. Provisional Patent Application Ser. No. 60/488,323, filed Jul. 18, 2003, and U.S. Provisional Patent Application Ser. No. 60/488,590, filed Jul. 18, 2003. The content of each application above is hereby incorporated by reference herein in its entirety.

TECHNICAL FIELD

This invention relates to endoprotheses.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

Passageways containing endoprotheses can become re-occluded. Re-occlusion of such passageways is known as restenosis. It has been observed that certain drugs can inhibit the onset of restenosis when the drug is coated on the endoprosthesis.

SUMMARY

Generally, the invention relates to a coated endoprosthesis. The endoprosthesis may be, e.g., a metal or a metal alloy stent. The coating may include a therapeutic agent, e.g., a restenosis inhibiting agent, and may degrade in biological systems.

In one aspect, the invention features an implantable endoprosthesis including a tubular member having a coating. The coating includes a polymeric material that includes a reaction product of a polyol, an isocyanate and a silsesquioxane having at least two pendent hydroxyl groups.

In some embodiments, the coating includes a therapeutic agent. The coating includes, e.g., between about 1 percent by weight and about 35 by weight therapeutic agent or between about 5 percent by weight and about 25 by weight therapeutic agent. In a specific embodiment, the therapeutic agent inhibits restenosis. An example of such a therapeutic agent is paclitaxel.

The polymeric material can be configured to fully release its therapeutic agent in less than seven days in blood at body temperature and/or to degrade in less than 365 days in blood at body temperature.

Polyols include, e.g., polyethylene glycol, polycaprolactone, polycyclooctene, trans-1,4 butadiene, transisoprene, polynorbornene and polymethacrylate copolymer, polycaprolactone-polylactide copolymer, polycaprolactone-polyglycolide copolymer, polycaprolactone-polylactide-polyglycolide copolymer, polylactide, polycaprolactone-poly(β-hydroxybutyric acid) copolymer, poly(β-hydroxybutyric acid) or mixtures of these polyols.

In a specific embodiment, the polyol has only two pendent hydroxyl groups, and the hydroxyl groups are disposed at ends of the polyol.

The isocyanate can be, e.g., a diisocyanate, e.g., 4,4' diphenyl methylene diisocyanate, toluene-2,4-diisocyanate, toluene-2,6-diisocyanate, hexamethylene-1,6-diisocyanate, 4,4'-diphenylmethane diisocyanate, isophorone diisocyanate, and hydrogenated 4,4'-diphenylmethane diisocyanate or mixtures of these.

The silsesquioxane can be, e.g., 1-(2-trans-cyclohexanediol)ethyl-3,5,7,9,11,13,15-isobutylpentacyclo-[9.5.1.1$^{3,9}$.1$^{5,15}$.1$^{7,13}$]octasiloxane, 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]propane-1,3-diol, 1-(2,3-propanediol)propoxy-3,5,7,9,11,13,15-isobutylpentacyclo-[9.5.1.1$^{3,9}$.1$^{5,15}$.1$^{7,13}$]octasiloxane, 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol or mixtures of these.

In some embodiments, a weight ratio of the polyol to the silsesquioxane is from about 1:2 to about 1:30, or from about 1:5 to about 1:25.

The coating can have a thickness, e.g., of between about 3 micron and about 150 micron before the implantable endoprosthesis is expanded or between about 20 micron and 50 micron before the implantable endoprosthesis is expanded.

A coverage of the polymeric material on the tubular member can be, e.g., from about 0.5 μg per square millimeter of surface area of the tubular member to about 10 μg per square millimeter of surface area of the tubular member.

The tubular member can include, e.g., an alloy, a bioresorbable metal, a metal oxide, a bioresorbable polymer or mixtures of these. In specific embodiments, the material is nitinol.

In some embodiments, the polymeric material is a thermoplastic and has an absolute molecular weight of greater than about 50,000, e.g., greater than about 100,000, greater than about 150,000 or greater than about 250,000.

In a specific embodiment, the polyol includes a polycaprolactone-polylactide copolymer, and the silsesquioxane includes 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol.

The polyol can have, e.g., an absolute molecular weight of from about 5,000 to about 50,000, from about 5,000 to about 25,000 or from about 10,000 to about 20,000.

In some embodiments, the polymeric material has a glass transition temperature of less than 100° C. In a specific embodiment, the polymeric material has a glass transition temperature of within about 10° C. of nominal human body temperature or within about 20° C. of nominal human body temperature.

The polymeric material can have, e.g., a storage modulus at 25° C. of less than 1,000 MPa, e.g., less than 750 MPa, less than 600 MPa or less than 500 MPa.

In another aspect, the invention features a method of treating a cavity or lumen in a mammal. The method includes inserting, into the lumen or cavity of the mammal, an implantable endoprosthesis including a tubular member having a coating. The coating includes a polymeric material that includes a reaction product of a polyol, an isocyanate and a silsesquioxane having at least two pendent hydroxyl group. The implantable endoprosthesis is expanded within the cavity or lumen of the mammal.

In some embodiments, the expanding is performed with a balloon in a vascular lumen.

In another aspect, the invention features a method of making a implantable endoprosthesis that includes a tubular member. The method includes coating the tubular member with a polymeric material that includes a reaction product of a polyol, an isocyanate and a silsesquioxane having at least two hydroxyl groups.

In some embodiments, the coating also includes a therapeutic agent.

The coating can be applied, e.g., by spraying a solution of the polymeric material onto the tubular member. The solution can contain, e.g., less than about 10 percent by weight of the polymeric material in a solvent. The solvent can be, e.g., tetrahydrofuran, toluene, methylene chloride or mixtures of these solvents.

In another aspect, the invention features an implantable endoprosthesis that includes a tubular member that is expandable from a first size to a second size and has a coating that includes a polymeric material and a therapeutic agent. During expansion of the implantable endoprosthesis from a first size to a second size, the coating does not substantially crack.

In some embodiments, the polymeric material includes a reaction product of a polyol, an isocyanate and a silsesquioxane having at least two pendent hydroxyl groups.

The tubular member can be, e.g., formed from a metal.

In another aspect, the invention features an implantable endoprosthesis that includes a tubular member that has a coating that includes a polymeric material and a therapeutic agent. During routine chemical sterilization of the implantable endoprosthesis with ethylene oxide, the coating does not slough off the tubular member.

The tubular member can be, e.g., a stent formed from a metal.

The polymeric material can include, e.g., a reaction product of a polyol, an isocyanate and a silsesquioxane having at least two pendent hydroxyl groups.

In another aspect, the invention features an implantable endoprosthesis that includes a tubular member that has a coating that includes a polymeric material that includes a reaction product of a polyol and an isocyanate.

In some embodiments, the reaction product also includes a silsesquioxane that has at least two pendent hydroxyl groups.

The coating can include a therapeutic agent.

In another aspect, the invention features an implantable endoprosthesis that includes a polymeric material that includes a reaction product of a polyol, an isocyanate and a silsesquioxane having at least two pendent hydroxyl groups. For example, the implantable endoprosthesis can include a tubular member, and the polymeric material can form a coating on the tubular member. In some embodiments, the tubular member is formed from a metal, e.g., one that degrades or corrodes in biological systems. For example, the metal that is degradable in biological systems can be magnesium or a magnesium alloy.

In another aspect, the invention features an implantable endoprosthesis that includes a tubular member. The tubular member includes a polymeric material that includes a reaction product of a polyol, a silsesquioxanes and an isocyanate. In some embodiments, the polymeric may include therapeutic agent dispersed therein.

Embodiments may have one or more of the following advantages. The coatings are flexible and resilient, enabling expansion of an implantable endoprosthesis having the coating from a first size to a second size larger than the first size without the coating substantially deforming, cracking and/or peeling during and/or after the expansion. The coatings can envelope a variety of materials, including metals, metal alloys, polymers and polymer alloys. The coatings allow for controlled release of therapeutic agents, e.g., paclitaxel. The rate of release of the therapeutic agent and/or the rate of degradation of the coating in biological systems can be controlled, and in many cases, predetermined, by adjusting ratios of the reaction products from which the coating is formed. The coatings are resistant to damage from sterilants, e.g., chemical sterilants, e.g., ethylene oxide; for example, coatings do not slough off the during routine chemical sterilization.

The term "polyol" as used herein includes any organic compound having on average two or more hydroxyl groups.

All publications, patent applications, patents, and other references mentioned herein are incorporated by reference in their entirety.

Other aspects, features, and advantages will be apparent from the description and drawings, and from the claims.

DETAILED DESCRIPTION

Figure 1:
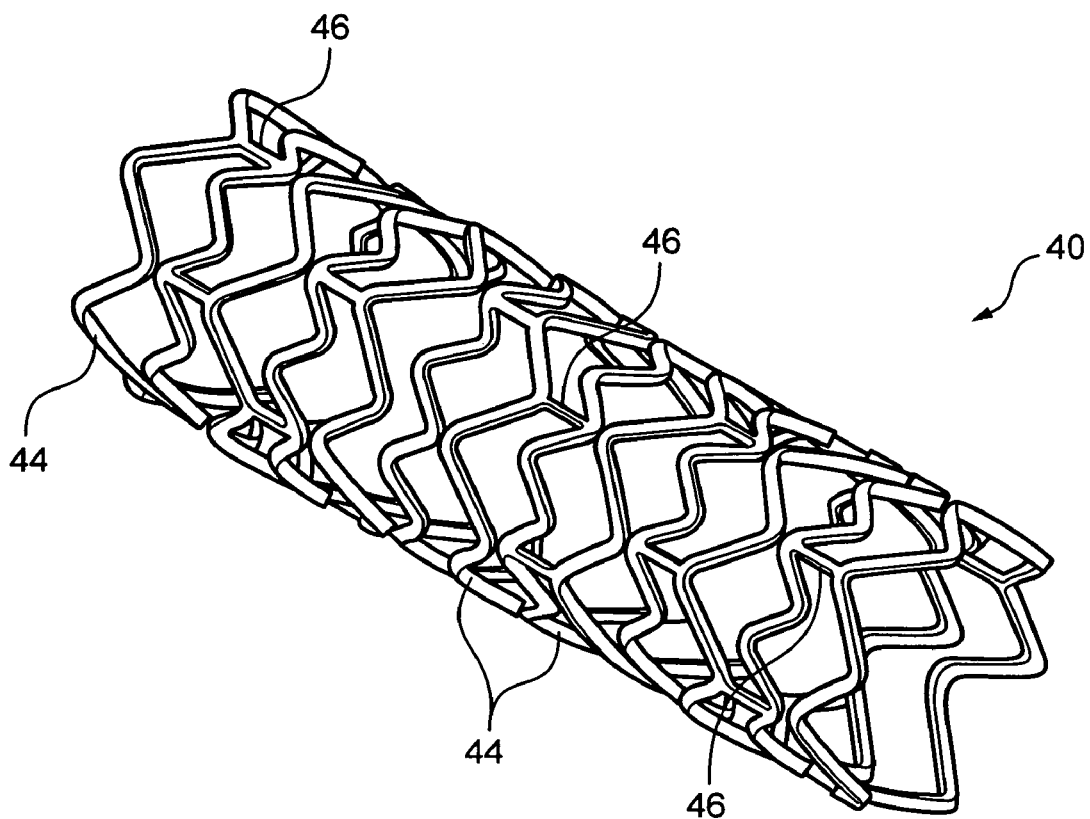
FIG. 1 is a perspective view of a metal stent having a coating.

Referring to FIG. 1, a stent 40 includes bands 44 and connectors 46 that extend between and connect adjacent bands. During use, stent 40 is expanded from an initial, smaller transverse dimension to a larger transverse dimension to contact a wall of a lumen. Stent 40 is formed from a metal or a metal alloy, e.g., stainless steel, titanium, tantalum or Nitinol, and has a coating 14 that includes a therapeutic agent and a polymeric material that degrades in biological systems. The polymeric material includes a reaction product of a polyol, an isocyanate and a silsesquioxane having at least two pendent hydroxyl groups.

The polyol can be degradable, non-degradable, crystalline, partially crystalline or amorphous. The polyol can be, e.g., polyethylene glycol (PEG) polyol, polytetramethylene glycol polyol (polyTHF), polycyclooctene (PCO) polyol, trans-1,4-butadiene polyol, transisoprene polyol, polycaprolactone (PCL) polyol, polycaprolactone-polylactide copolymer polyol, e.g., polycaprolactone-polylactide random copolymer polyol, polycaprolactone-polyglycolide copolymer polyol, e.g., polycaprolactone-polyglycolide random copolymer polyol, polycaprolactone-polylactide-polyglycolide copolymer polyol, e.g., polycaprolactone-polylactide-polyglycolide random copolymer polyol, polylactide polyol, polycaprolactone-poly(β-hydroxybutyric acid) copolymer polyol, e.g., polycaprolactone-poly(β-hydroxybutyric acid) random copolymer polyol, poly(β-hydroxybutyric acid) polyol, polyester polyols, polyamide polyols, polyimide polyols, polyacrylate and polymethacrylate polyols, e.g., hydroxyl-terminated polyacrylate homopolymers and copolymers, polymethacrylate homopolymers and copolymers, (e.g., copolymers of methyl acrylate or methyl methacrylate and ethyl, propyl, or butyl acrylate or methacrylate), propane diols, butane diols, 1,6-hexanediol, 1,8-octanediol, neopentylglycol, glycerol, trimethylol propane, pentaerythritol, quinitol, mannitol, sorbitol, 1,4-trans-cyclohexane exodiol and 1,4-trans-cyclohexane endodiaol.

Polycaprolactone (PCL) polyols can be prepared, e.g., by initiating polymerization of caprolactone with a low molecular weight diol. Examples of low molecular weight diol initiators include C1-C10 alkyl diols, e.g., propane diol, butane diol or hexane diol.

Polycyclooctene (PCO) polyol, trans-1,4-butadiene polyol and transisoprene polyol can be made, e.g., by methods disclosed in European Polymer Journal, vol. 31, page 51 (1995) and European Polymer Journal, vol. 31, page 339 (1997). Sartomer Company commercially provides a number of poly (diene) polyols, e.g., polybutadiene polyol.

Hydroxyl group functionalized polyacrylate and polymethacrylate polymers can be made, e.g., by methods disclosed in Macromolecules, vol. 37, pages 9694-9700 (2004).

Mixtures of polyols can be used.

In some embodiments, the polyol has only two pendent hydroxyl groups, and the hydroxyl groups are disposed at ends of the polyol.

The polyol can, e.g., have an absolute molecular weight of from about 5,000 to about 250,000, e.g., from about 5,000 to about 100,000 or from about 5,000 to about 80,000.

Isocyanates can be, e.g., aliphatic, cycloaliphatic, aromatic, or heterocyclic. For example, isocyanates include C4-C30 linear or branched alkyl diisocyanates and C8-C30 aryl diisocyanates. Optionally the alkyl or aryl groups can be substituted with one or more substituents such as C4-C10 tertiary alkyl, C1-C12 primary or secondary alkyl, C4-C10 tertiary alkoxy, C1-C12 primary or secondary alkoxy. The alkyl or aryl groups can also be substituted with a halogen, e.g., chlorine or bromine. Some specific isocyanates include 4,4'-diphenyl methylene diisocyanate, toluene-2,4-diisocyanate (TDI), toluene-2,6-diisocyanate, hexamethylene-1,6-diisocyanate (HDI), isophorone diisocyanate (IPDI), hydrogenated 4,4'-diphenylmethane diisocyanate, 1,3-bisisocyanato-1-methylene ethylene benzene, ethylene diisocyanate, tetramethylene-1,4-diisoyanate, dodecane-1,12-diisocyanate, cyclobutane-1,3-diisocyanate, naphthylene-1,5-diisocyanate and triphenylmethane-4,4',4"-triisocyanate.

Mixtures of isocyanates can be used.

Figure 2:
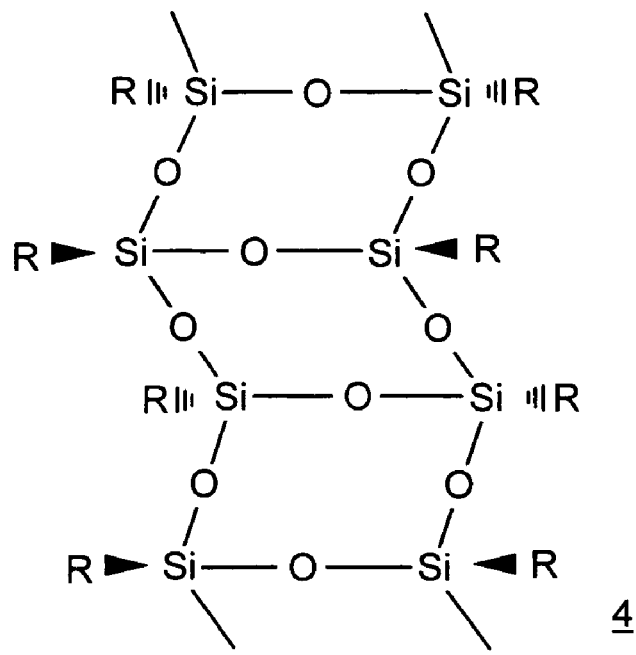
FIGS. 2, 3 and 4 represent ladder-type 4, T$_8$ cube-type 5 and cage-type 6 silsesquioxane structures, respectively.
Figure 3:
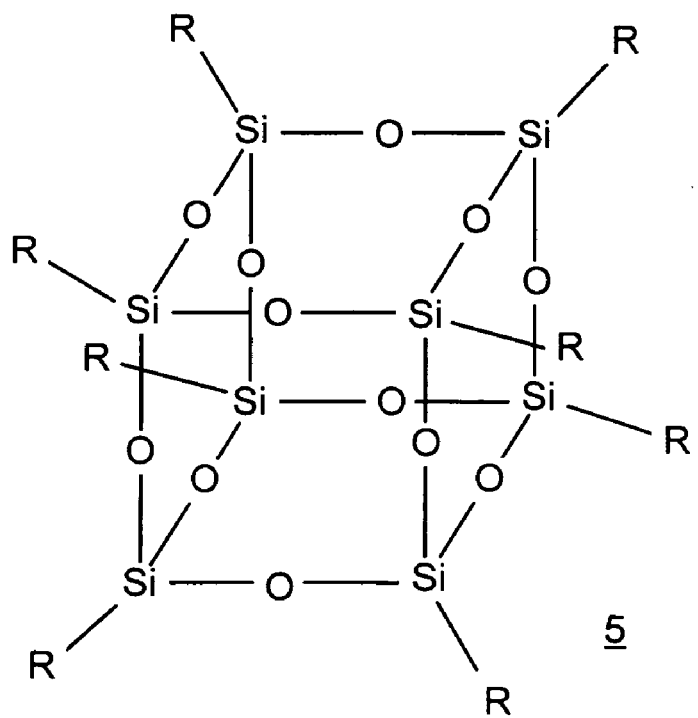
Figure 4:
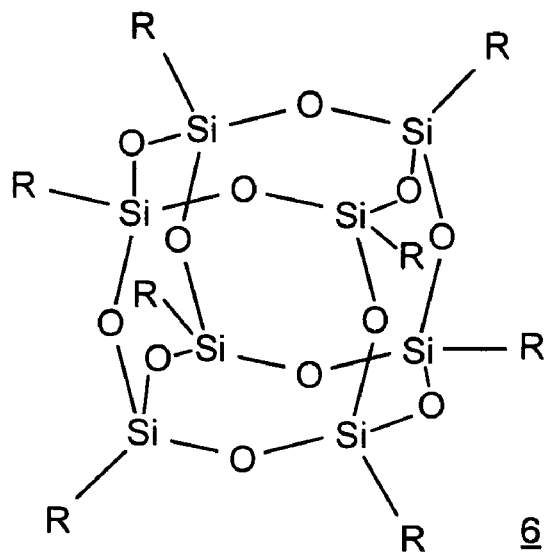

Referring to FIGS. 2-4, silsesquioxanes, also known as T-resins, can exist in a variety of structural configurations, including ladder-type structures 4 (FIG. 2), T$_8$ cube-type structures 5 (FIG. 3) and cage-type structures 6 (FIG. 4). Many silsesquioxanes are commercially available from either Hybrid Plastics™, Aldrich Chemical or from Reade Advanced Materials. Silsesquioxanes are discussed in "Silsesquioxanes, Bridging the Gap Between Polymers and Ceramics", Chemfiles, Vol. 1, No. 6, 2001 (Aldrich Chemical), the entire contents of which is hereby incorporated by reference herein.

Figure 5:
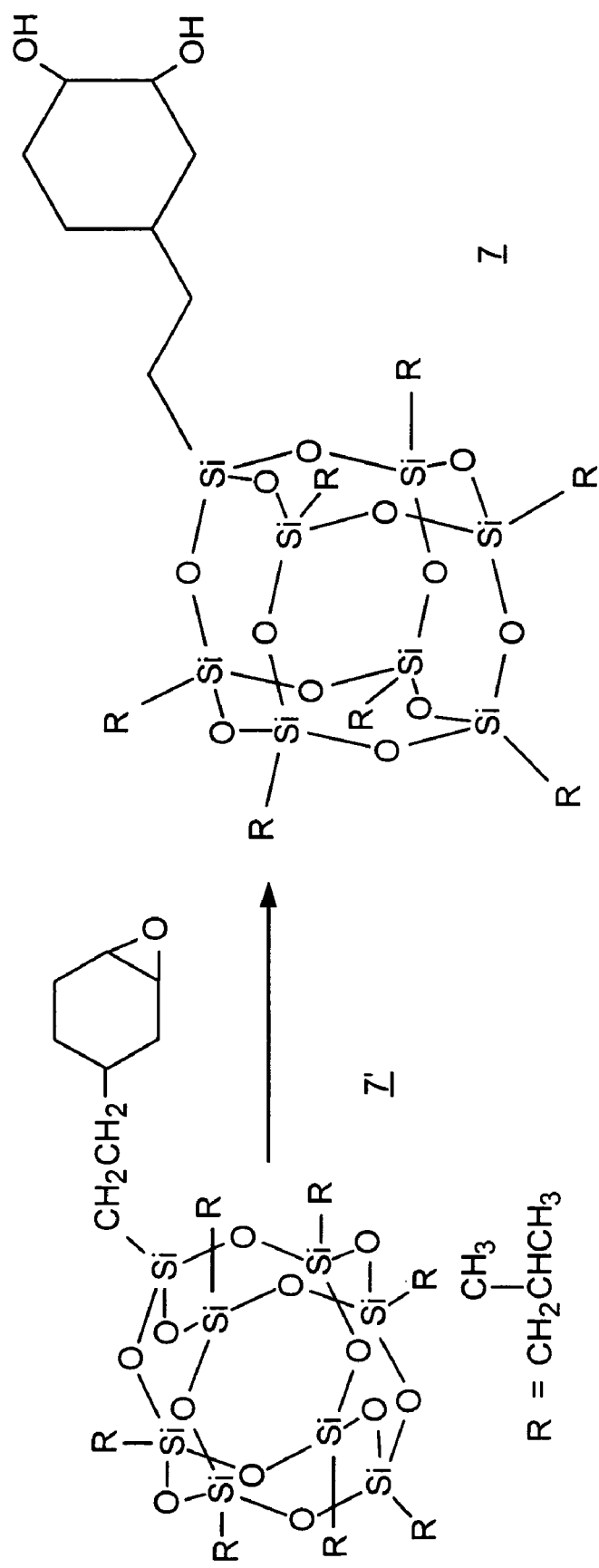
FIG. 5 is a reaction scheme illustrating a method of preparing 1-(2-trans-cyclohexanediol)ethyl-3,5,7,9,11,13,15-isobutylpentacyclo-[9.5.1.1$^{3,9}$.1$^{5,15}$.1$^{7,13}$]-octasiloxane 7 from the corresponding epoxide, 1-[2-(3,4-epoxycyclohexyl)ethyl]-3,5,7,9,11,13,15-isobutylpentacyclo-[9.5.1.1$^{3,9}$.1$^{5,15}$.1$^{7,13}$]octasiloxane 7'.

Referring to FIG. 5, one silsesquioxane is 1-(2-trans-cyclohexanediol)ethyl-3,5,7,9,11,13,15-isobutylpentacyclo-[9.5.1.1$^{3,9}$.1$^{5,15}$.1$^{7,13}$]octasiloxane 7. It can be prepared from the corresponding epoxide, 1-[2-(3,4-epoxycyclohexyl)ethyl]-3,5,7,9,11,13,15-isobutylpentacyclo-[9.5.1.1$^{3,9}$.1$^{5,15}$.1$^{7,13}$]octasiloxane 7' by hydrolysis.

Figure 6:
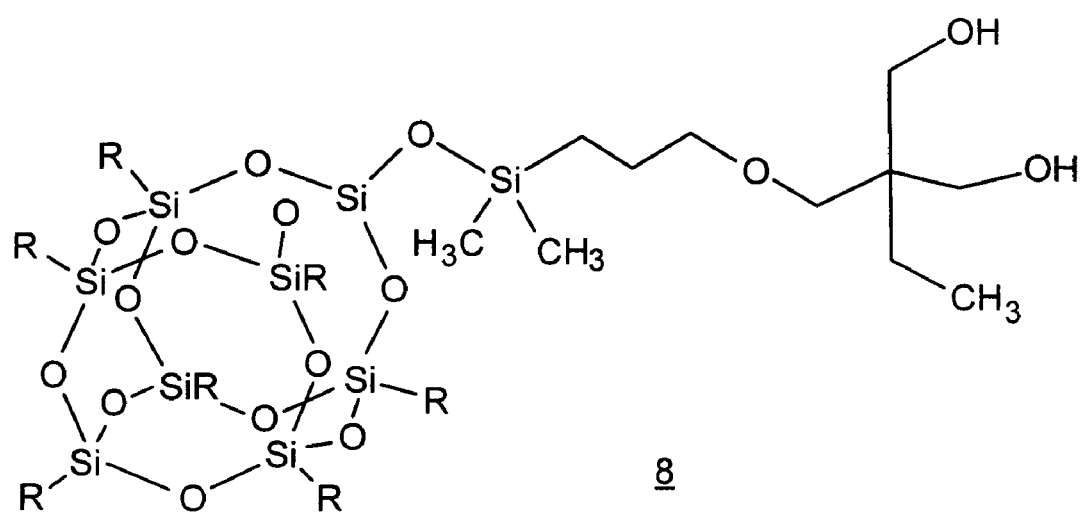
FIG. 6 is a structure of 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol 8.

Referring now to FIG. 6, another silsesquioxane 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol 8.

Figure 7:
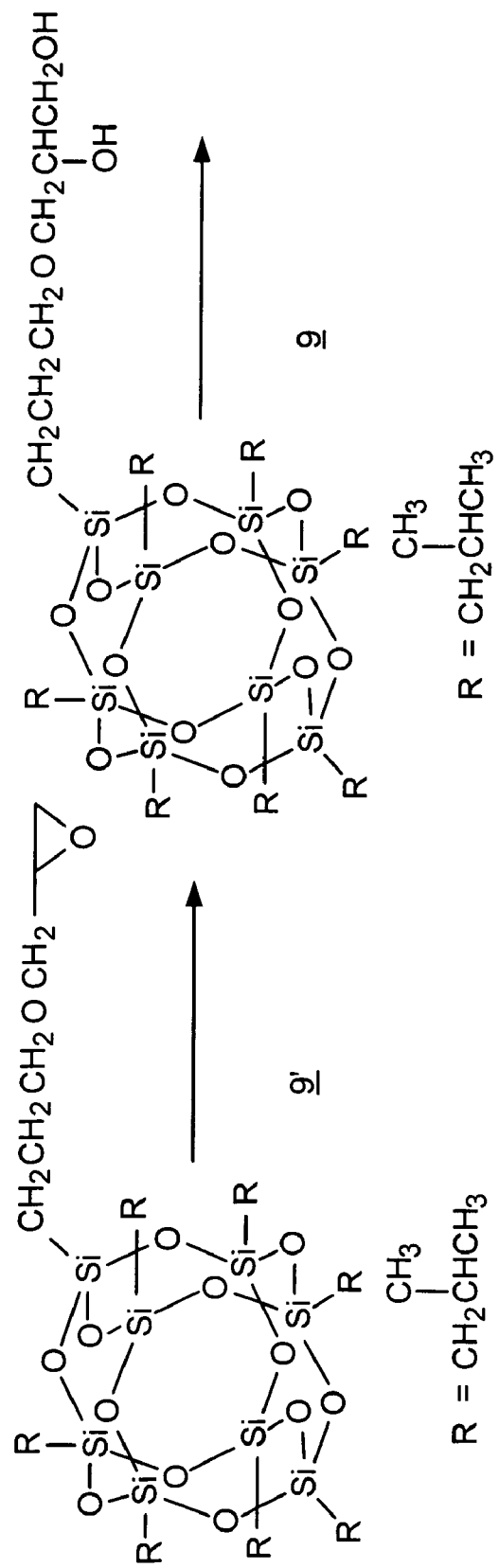
FIG. 7 is a reaction scheme illustrating a method of preparing 1-(2,3-propanediol)propoxy-3,5,7,9,11,13,15-isobutylpentacyclo[9.5.1.1$^{3,9}$.1$^{5,15}$.1$^{7,13}$]-octasiloxane 9 from the corresponding epoxide, 1-(3-glycidyl)propoxy-3,5,7,9,11,13,15-isobutylpentacyclo-[9.5.1.1$^{3,9}$.1$^{5,15}$.1$^{7,13}$]octasiloxane 9'.

Referring to FIG. 7, another silsesquioxane is 1-(2,3-propanediol)propoxy-3,5,7,9,11,13,15-isobutylpentacyclo-[9.5.1.1$^{3,9}$.1$^{5,15}$.1$^{7,13}$]octasiloxane 9. It can be made from the corresponding epoxide, 1-(3-glycidyl)propoxy-3,5,7,9,11,13,15-isobutylpentacyclo-[9.5.1.1$^{3,9}$.1$^{5,15}$.1$^{7,13}$]octasiloxane 9'.

Figure 8:
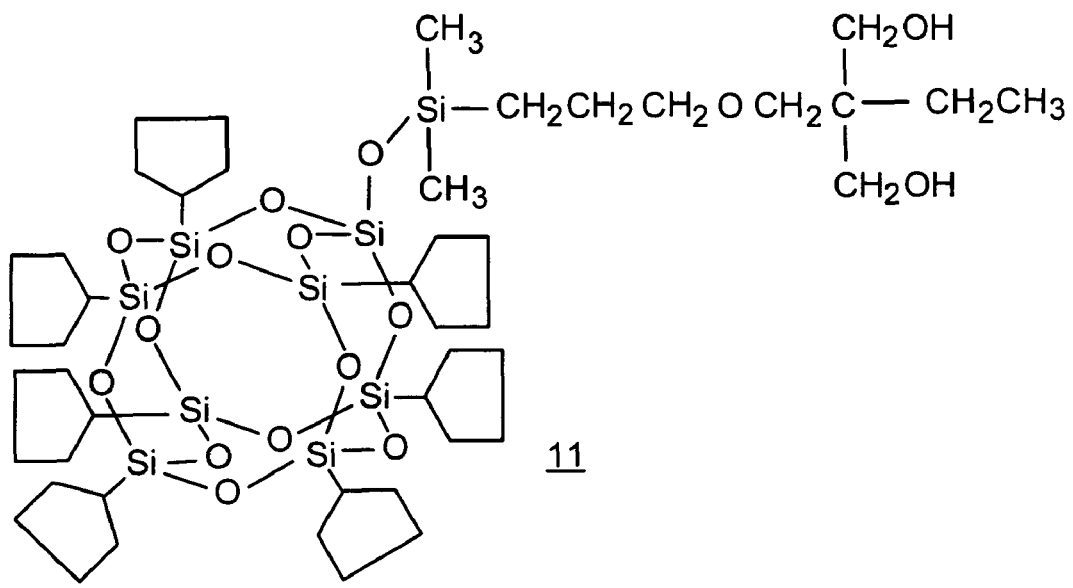
FIG. 8 is a structure of 2-ethyl-2-[[3-[[(heptacyclopentylpentacyclo-[9.5.1.1$^{3,9}$.1$^{5,15}$.1$^{7,13}$]octasiloxanyl)oxy]dimethylsilyl]propoxy]methyl]propane-1,3-diol 11.
Figure 9:
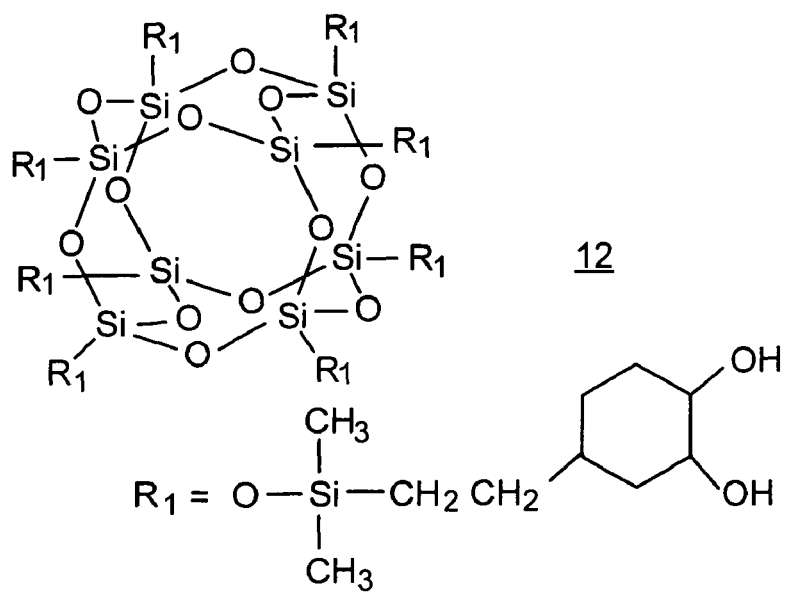
FIG. 9 is a structure of a silsesquioxane 12 having 16 hydroxyl groups per molecule.

FIG. 8 shows another silsesquioxane, namely, 2-ethyl-2-[[3-[[(heptacyclopentylpentacyclo-[9.5.1.1$^{3,9}$.1$^{5,15}$.1$^{7,13}$]octasiloxanyl)oxy]-dimethylsilyl]propoxy]methyl]propane-1,3-diol 11. FIG. 9 illustrates a silsesquioxane 12 that has 16 hydroxyl groups per molecule.

Mixtures of silsesquioxanes can be used.

Figure 10:
FIG. 10 is a reaction scheme illustrating a possible method of preparing partially condensed silsesquioxanes 2 and fully condensed silsesquioxanes 3 from an organo-trihydroxy silane 1.

Referring to FIG. 10, one method of producing silsesquioxanes is via hydrolytic condensation of trifunctional organosilicon compounds, e.g., trihaloalkyl silanes or trialkoxyalkyl silanes. Hydrolysis of the trifinctional organosilicon compounds gives trihydroxy silanes 1, which upon condensation gives incompletely-condensed silsesquioxanes 2, which can be represented by formula $[RSiO_{3/2}]_n(H_2O)_{3n/2-x}$. Further condensation of 2 gives fully condensed silsesquioxanes 3, represented by formula $[RSiO_{3/2}]_n$.

The polymers can be synthesized, e.g., by a one-step condensation polymerization as described in "Shape Memory Polymers Based On Semicrystalline Thermoplastic Polyurethanes Bearing Nanostructured Hard Segments," U.S. patent application Ser. No. 11/111,388, filed concurrently herewith. Generally, the polymers are prepared by charging a flask that has been purged with an inert gas, e.g., nitrogen, with the polyol. To the polyol is added a selected silsesquioxane in a solvent, e.g., toluene. The polyol-silsesquioxane mixture is heated to approximately 50-80° C. and maintained at that temperature. A selected isocyanate or mixture of isocyanates is/are added together with a catalyst, e.g., dibutyltin dilaurate. Temperature is maintained with stirring. Over time, the reaction mixture thickens. In a typical embodiment, the reaction mixture is maintained at the reaction temperature for 2 to 3 hours. In a typical embodiment, the thickened polymer solution is purified by precipitation by pouring the mixture into n-hexane.

Figure 11:
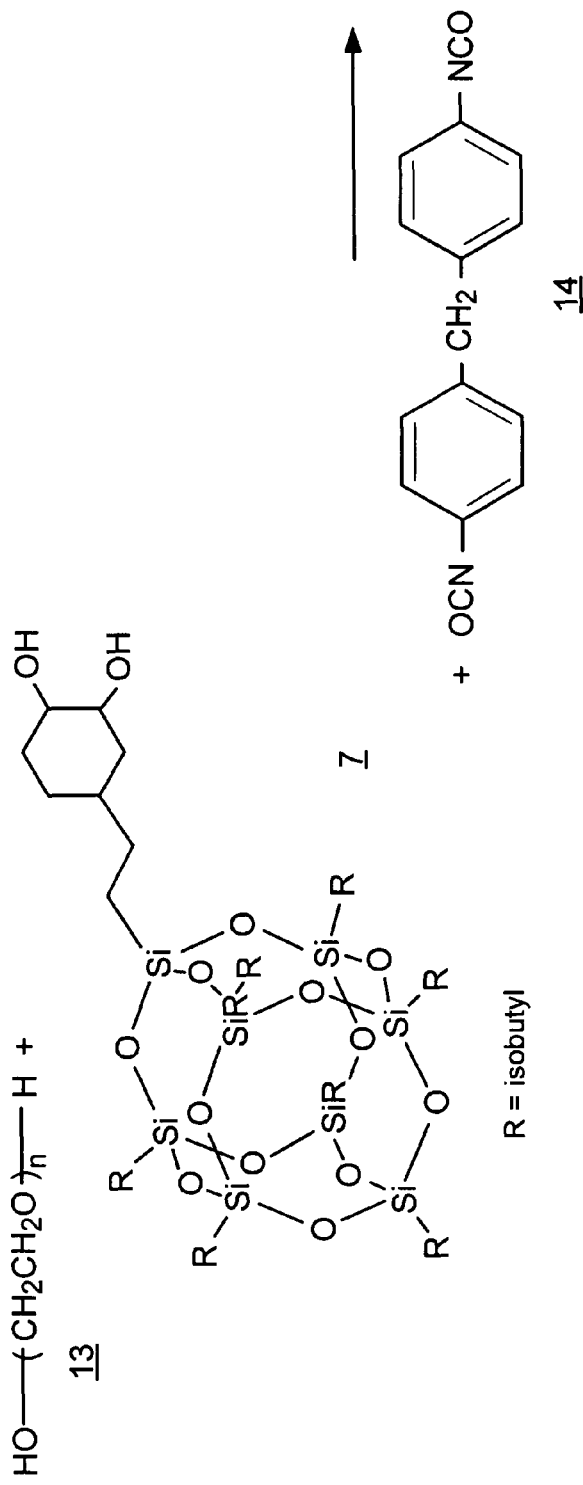
FIG. 11 is a reaction scheme for producing a polymeric material from reacting polyethylene glycol 13, 1-(2-trans-cyclohexanediol)ethyl-3,5,7,9,11,13,15-isobutylpentacyclo-[9.5.1.1$^{3,9}$.1$^{5,15}$.1$^{7,13}$]octasiloxane 7 and 4,4'-diphenylmethylene diisocyanate 14.

Referring now to FIG. 11, in a specific embodiment, the polymeric material is prepared by reacting polyethylene glycol 13 together with 1-(2-trans-cyclohexanediol)ethyl-3,5,7,9,11,13,15-isobutylpentacyclo-[9.5.1.1$^{3,9}$.1$^{5,15}$.1$^{7,13}$]-octasiloxane 7 and 4,4' diphenyl methylene diisocyanate 14.

Figure 12:
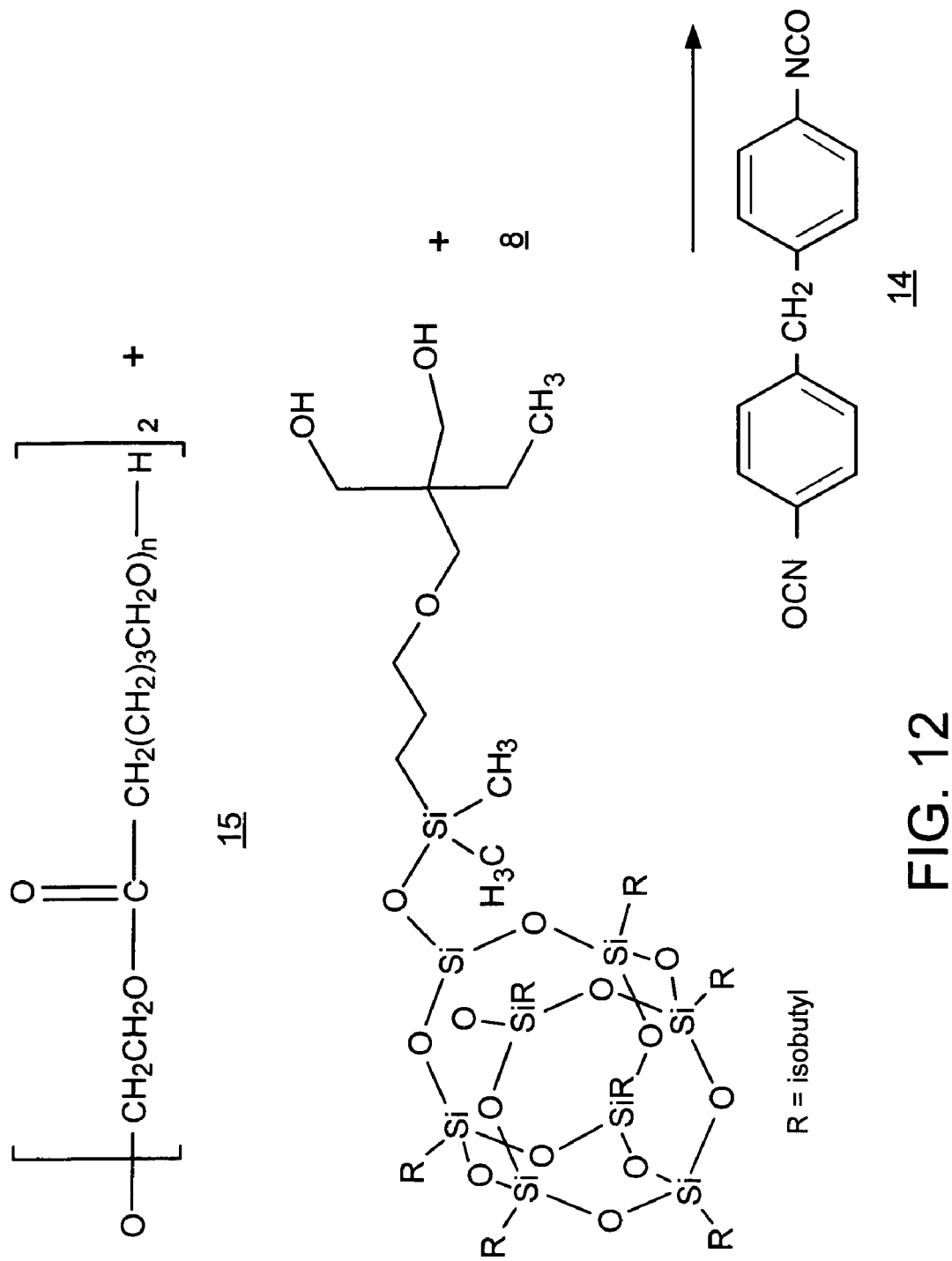
FIG. 12 is a reaction scheme for producing a polymeric material from reacting polycaprolactone diol 15, 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol 8 and 4,4'-diphenylmethylene diisocyanate 14.

Referring to FIG. 12, in another specific embodiment, the polymeric material is prepared by reacting polycaprolactone diol 15 together with 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol 8 and 4,4'-diphenylmethylene diisocyanate 14.

Figure 13:
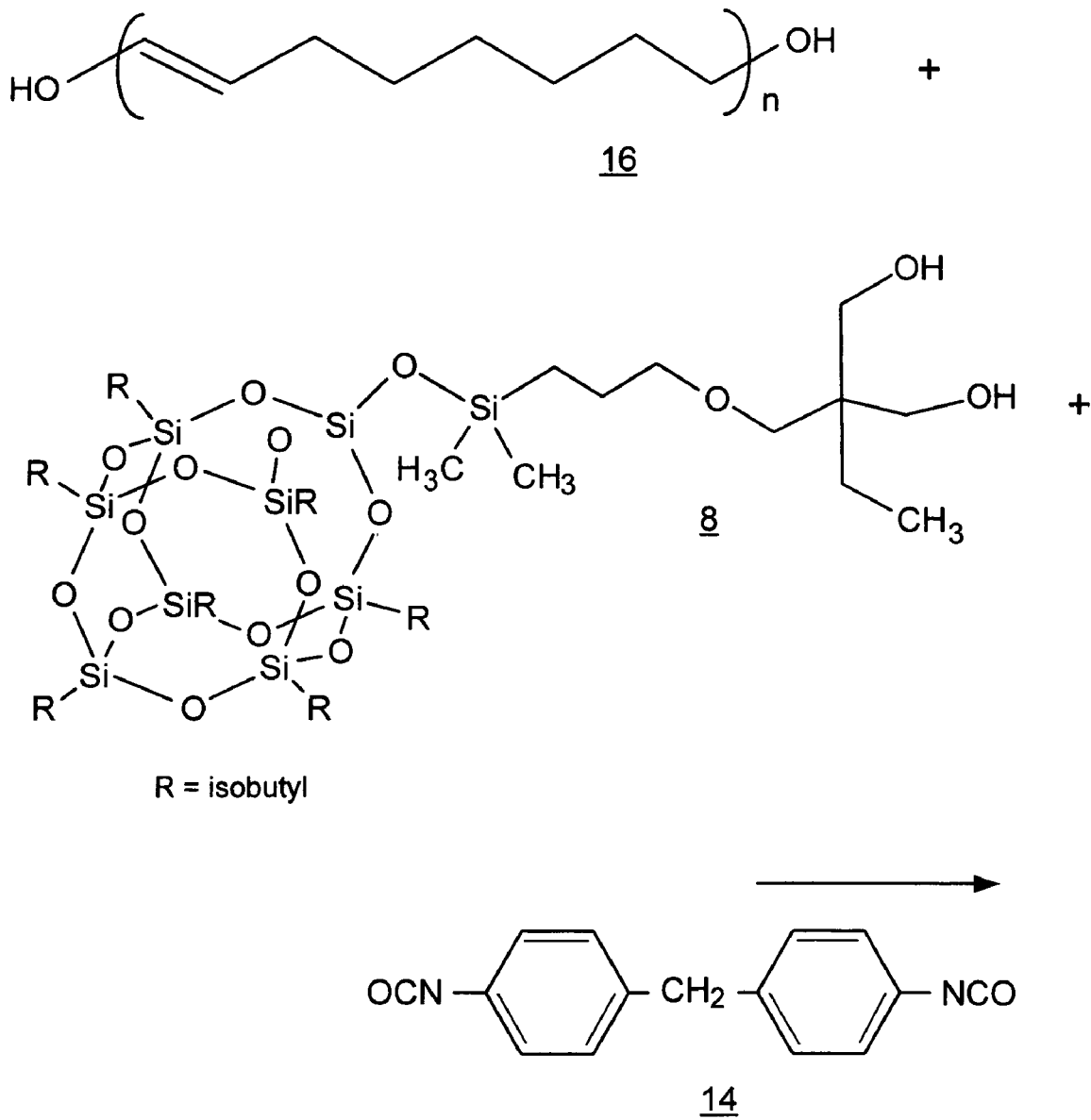
FIG. 13 is a reaction scheme for producing a polymeric material from reacting polycyclooctene diol 16, 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol 8 and 4,4'-diphenylmethylene diisocyanate 14.

Referring to FIG. 13, in another specific embodiment, the polymeric material is prepared by reacting polycyclooctene diol 16 together with 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol 8 and 4,4'-diphenylmethylene diisocyanate 14.

Figure 14:
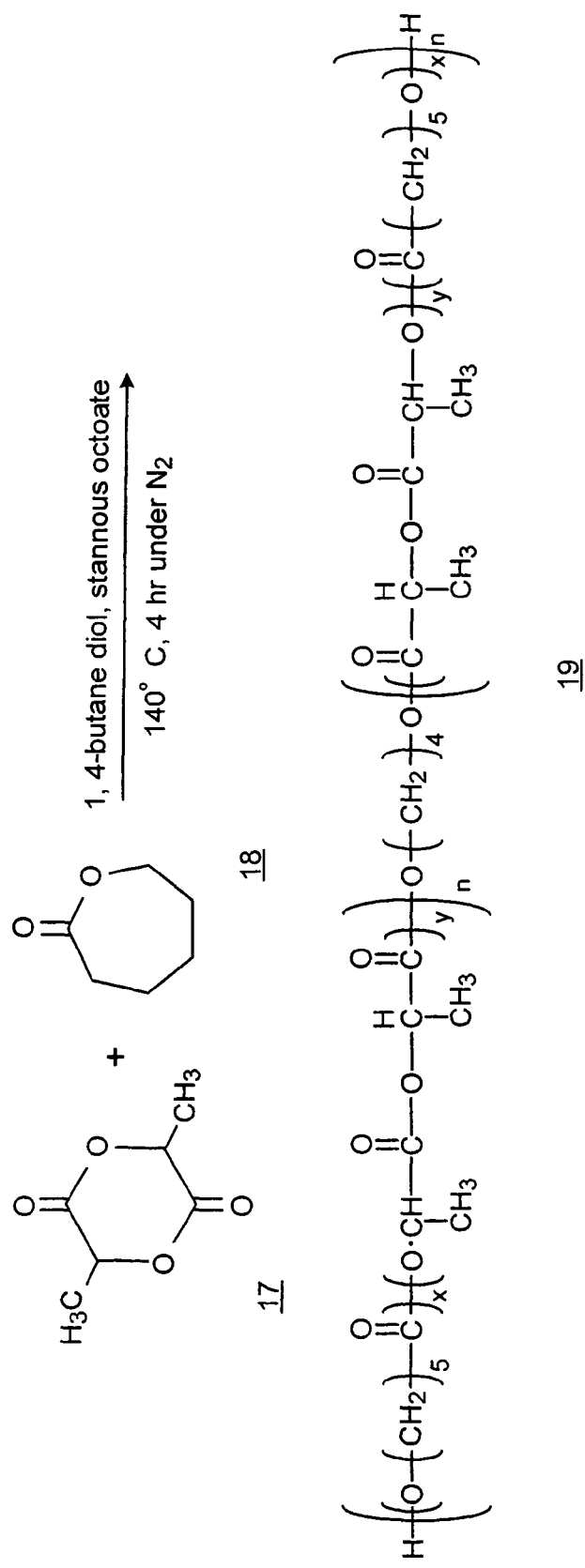
FIG. 14 is a reaction scheme for producing a polycaprolactone-polylactide random copolymer 19 from lactide 17 and caprolactone 18.
Figure 15:
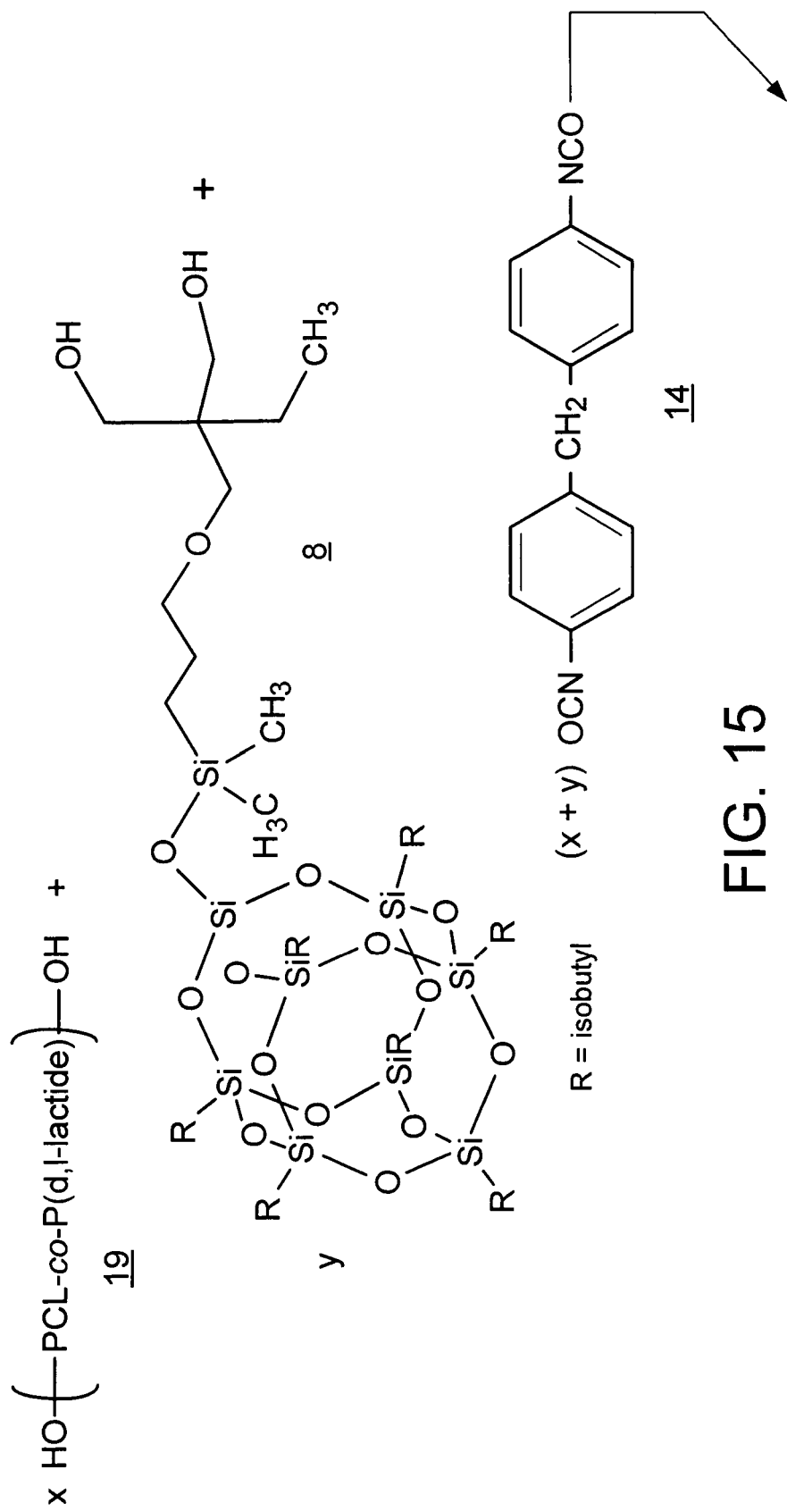
FIG. 15 is a reaction scheme for producing a polymeric material from reacting the polycaprolactone-polylactide random copolymer 19 of FIG. 15, 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol 8 and 4,4'-diphenylmethylene diisocyanate 14.
Figure 16:
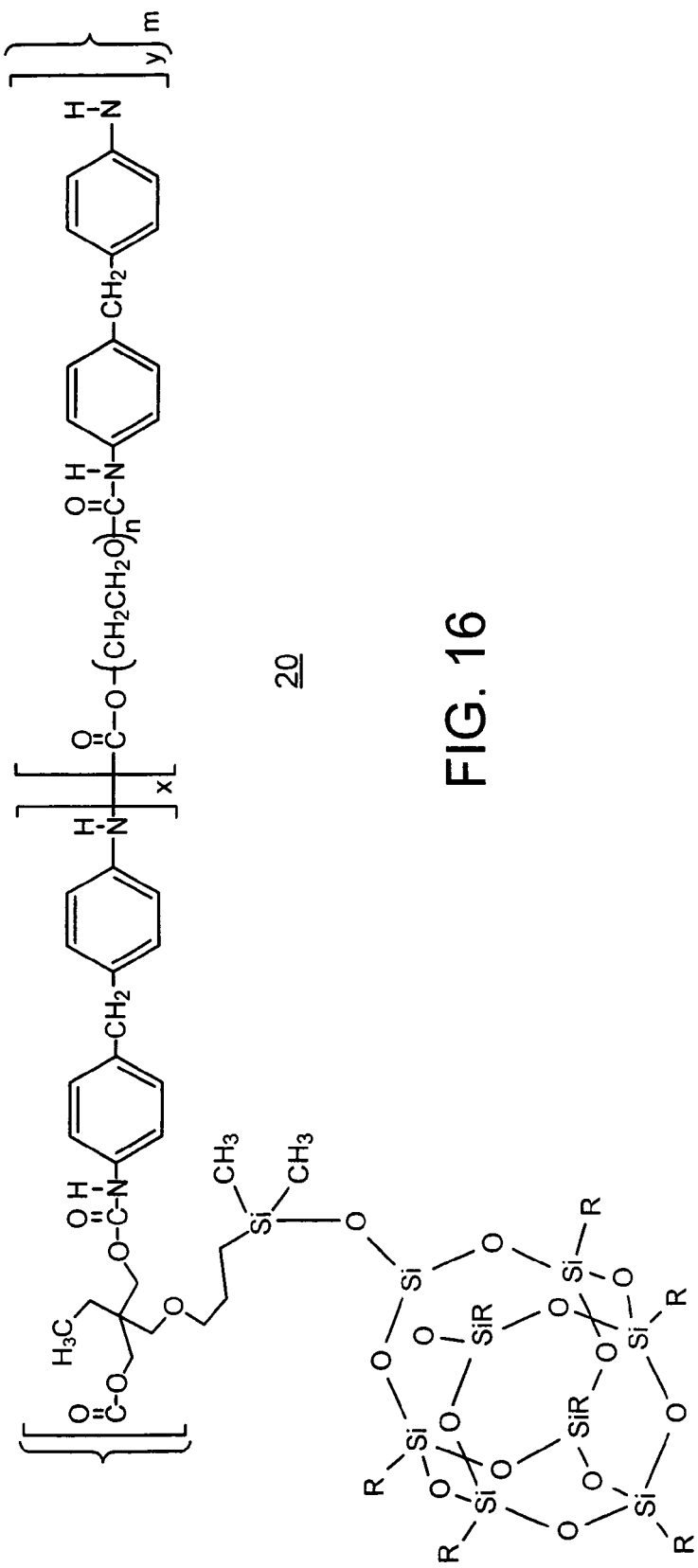
FIG. 16 is a possible reaction product 20 of the reaction scheme shown in FIG. 15.

Referring to FIGS. 14-16, a polycaprolactone-polylactide random copolymer 19 can be prepared by ring-opening condensation of D,L-lactide (meso) 17 and caprolactone 18. Random copolymer 19 can then be reacted together with 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol 8 and 4,4'-diphenylmethylene diisocyanate 14 to produce polymer 20 (FIG. 16). The polymer system enables systematic variation of ratio x/y, polyol degree of polymerization and total polymerization. For example, the ratio x/y can be between about 1 and about 20, the polyol degree of polymerization can be between about 2 and about 1000, and the total polymerization can be between about 3 to about 1000.

In general, the mole ratio of polyol to silsesquioxane to isocyanate can be, e.g., about 1:2:3, 1:5:6 or about 1:10:11. The weight ratio of the polyol to the silsesquioxane can be, e.g., from about 1:2 to about 1:30, from about 1:5 to about 1:25 or from about 1:5 to about 1:15.

In some embodiments, the polyol, the isocyante and/or the silsesquioxane is sufficiently hydrophilic so that the polymeric material forms a hydrogel when exposed to water.

The polymeric material can have, e.g., an absolute molecular weight of greater than about 25,000, e.g., greater than about 75,000, greater than about 85,000, greater than about 100,000, or greater than about 200,000. In some embodiments, the absolute molecular weight of the polymeric material is from about 25,000 to about 250,000, from about 25,000 to about 150,000 or from about 50,000 to about 150,000.

The polymeric material can have a polydispersity of, e.g., from about 1.1 to about 2.1, e.g., from about 1.3 to about 2.0, or from about 1.3 to about 1.8.

The polymeric material can be a thermoplastic or a thermoset.

In some embodiments, the polymers have a glass transition temperature of less than 100° C., e.g., less than 80° C., less than 65° C., less than 50° C., less than 45° C., less than 35° C., less than 30° C., less than 20° C., less than 10° C., less than 0° C., less than −25° C. or less than −50° C. In one specific embodiment, the polymers have a glass transition temperature of within 25° C. of nominal human body temperature or within 10° C. of nominal human body temperature.

The polymeric material has, e.g., a storage modulus at 25° C. of less than 1,500 MPa, e.g., less than 1,250 MPa, less than 1,000 MPa, less than 900 MPa, less than 800 MPa, less than 500 MPa or less than 250 MPa.

The rate of degradation of the polymeric material can be controlled by adjusting the amount and type of silsesquioxane used, and by the amount and type of polyol. For example, the degradation rate can be decreased by increasing the amount of silsesquioxane used in forming the polymer, or by increasing the molecular weight of the polyol in the polymer. On the other hand, the degradation rate can be increased by increasing the number of hydrolyzable groups in the polyol.

Generally, in-vitro degradation tests of the any of the above polymers can be performed by making approximately 150 micron thick films, and then immersing the films in 0.01 M phosphate buffer solution (PBS) containing 0.138 M NaCl and 0.0027 M KCl at 37° C. Degradation is measured gravimetrically by following the percent of film mass remaining with time.

Figure 17:
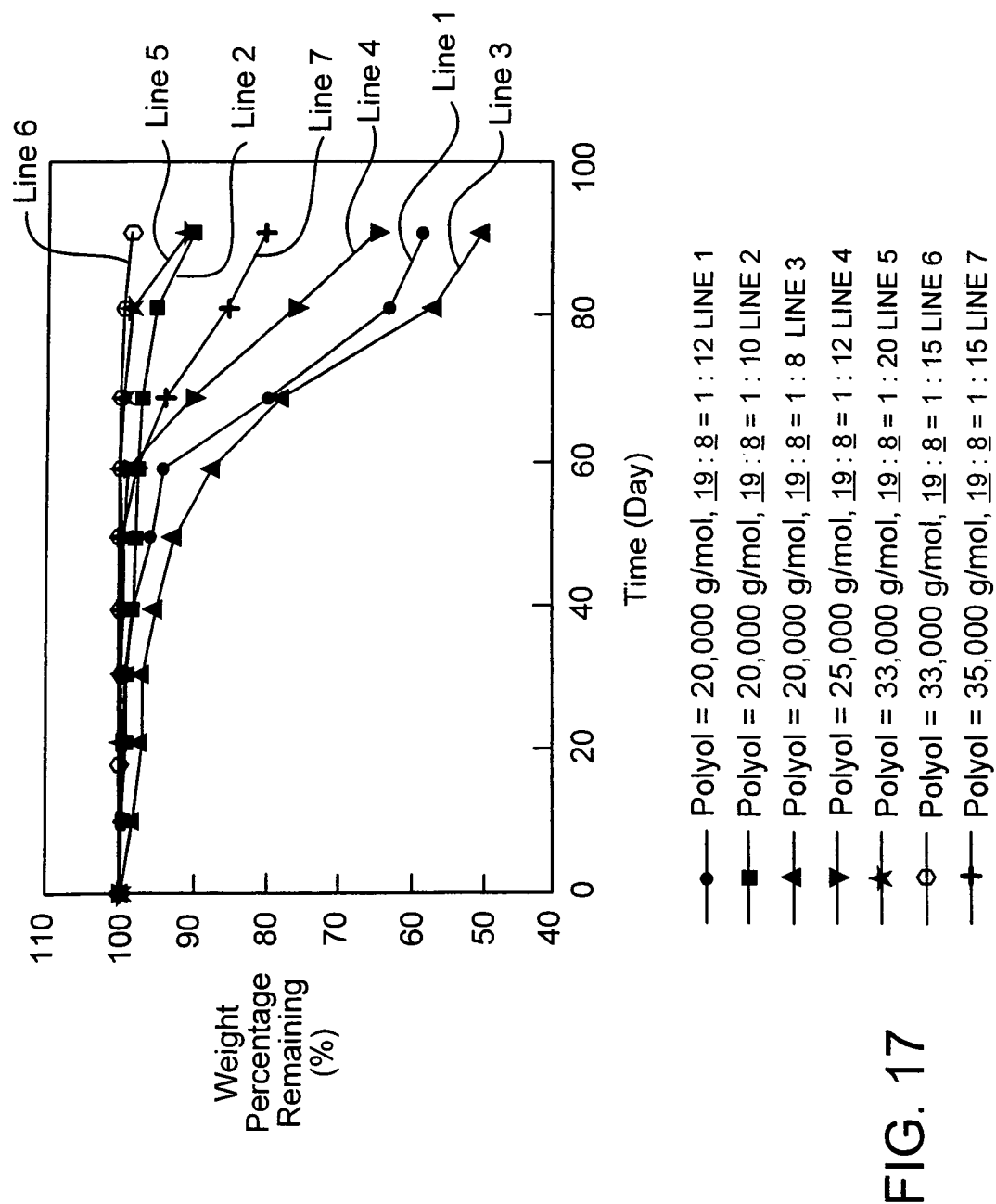
FIG. 17 is a graph of Weight Percentage Remaining Versus Time (days) for seven different polymeric materials in the form of films, the polymeric materials being formed from the reaction shown in FIG. 15.

FIG. 17 summarizes the results of degradation tests conducted on approximately 150 micron thick films of seven polymers formed by the reaction of polycaprolactone-polylactide random copolymer 19, together with 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol 8 and 4,4'-diphenylmethylene diisocyanate 14. The tests were conducted in 0.01 M phosphate buffer solution (PBS) containing 0.138 M NaCl and 0.0027 M KCl at 37° C. The results showed that the polymer made from 33,000 molecular weight copolymer 19 and having a ratio of 19 to 8 of 1 to 15 was the slowest to degrade (line 6), while the polymer made from 20,000 molecular weight copolymer 19 and having a ratio of 19 to 8 of 1 to 8 was the fastest to degrade (line 3). The graph generally verifies the trend that the degradation rate can be decreased by increasing the amount of silsesquioxane used in forming the polymer, or by increasing the molecular weight of the polyol in the polymer.

In general, the therapeutic agent can be a genetic therapeutic agent, a non-genetic therapeutic agent, or cells. Therapeutic agents can be used singularly, or in combination. Therapeutic agents can be, for example, nonionic, or they may be anionic and/or cationic in nature. A preferred therapeutic agent is one that inhibits restenosis. A specific example of one such therapeutic agent that inhibits restenosis is paclitaxel.

The therapeutic agent can also be used, e.g., to treat and/or inhibit pain, encrustation of the endoprosthesis or sclerosing or necrosing of a treated lumen.

Exemplary non-genetic therapeutic agents include: (a) anti-thrombotic agents such as heparin, heparin derivatives, urokinase, PPack (dextrophenylalanine proline arginine chloromethylketone), and tyrosine; (b) anti-inflammatory agents, including non-steroidal anti-inflammatory agents (NSAID), such as dexamethasone, prednisolone, corticosterone, budesonide, estrogen, sulfasalazine and mesalamine; (c) anti-neoplastic/antiproliferative/anti-miotic agents such as paclitaxel, 5-fluorouracil, cisplatin, vinblastine, vincristine, epothilones, endostatin, angiostatin, angiopeptin, rapamycin (sirolimus), biolimus, tacrolimus, everolimus, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines, (r) hormones; and (s) antispasmodic agents, such as alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, tropenzile, trospium chloride, xenytropium bromide, ketorolac, and pharmaceutically acceptable salts thereof.

Exemplary genetic therapeutic agents include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or micro particles, with and without targeting sequences such as the protein transduction domain (PTD).

Cells for use include cells of human origin (autologous or allogeneic), including whole bone marrow, bone marrow derived mono-nuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Any of the therapeutic agents described above can have more than a single function.

Generally, the coating includes, e.g., between about 1 percent by weight and about 35 by weight therapeutic agent, e.g., between about 5 percent by weight and about 30 percent by weight, between about 10 percent by weight and about 25 percent by weight or between about 15 percent by weight and about 20 percent by weight.

The coating can have a therapeutic agent elution profile that is, e.g., a function of the polymeric material. In particular, the elution profile can, e.g., be a function of the chemistry of the polymeric material, e.g., the monomers from which it is derived, the molecular weight of the polymeric material and a weight ratio of the monomers from which the polymeric material is derived. For example, in some embodiments, the rate of elution of the therapeutic agent from the coating can be a function of a ratio of the polyol component to the isocyanate portion. In some embodiments, adjusting the weight ratio of the monomers from which the polymeric material is derived enables "tuning" the elution rate to suite a particular need.

The coating can be configured to release substantially all of the therapeutic agent in a predetermined time. In some embodiments, the coating can be configured to release substantially all of the therapeutic agent in less than about 365 days, less than about 200 days, less than about 100 days, less than about 30 days, less than about 20 days, less than about 15 days or less than about 7 days while in blood at 37° C.

Coated tubular stent 40 can be made, e.g., by spraying a solution of the polymeric material onto an uncoated stent. Such spraying can be performed, e.g., during rotation of the stent to achieve a uniform coating thickness. The coating can be placed on by other methods, including dipping or electrostatically spraying.

The solution can, e.g., contain less than about 10 percent by weight of the polymeric material in a solvent. In some embodiments, the solution contains less than about 9 percent by weight, less than about 8 percent by weight, less than about 5 percent by weight, less than about 3 percent by weight, or less than about 1 percent by weight of the polymeric material in the solvent. Solvents include, e.g., tetrahydrofuran, toluene methylene chloride or mixtures of these solvents.

Coverage of the coating on the stent can be, e.g., from about 0.1 μg per square millimeter of surface area to about 10 μg per square millimeter of surface area. In some embodiments, the coverage is from about 0.5 μg to about 5 μg or from about 1 μg to about 2.5 μg.

In some embodiments, greater than 50 percent of the surface area of the stent is covered with coating 14, e.g., greater than 60 percent, greater than 75 percent, or greater than 90 percent of the surface area of the stent is covered with coating 14.

During expansion of the implantable endoprosthesis from an unexpanded size to an expanded size, the coating thins, but does not substantially crack. For example, before the stent 40 is expanded, the coating can have an average thickness of between about 5 μm and about 150 μm. In some embodiments, the coating has an average thickness of from about 10 μm to about 100 μm or from about 25 μm to about 75 μm.

In some embodiments, after expansion of stent 40 from the unexpanded size to the expanded size, the average thickness of the coating does not substantially decrease. While in other embodiment, after full expansion of stent 40 from the unexpanded size to the expanded size, the average thickness of coating decreases, e.g., by greater than about twenty percent. In some embodiments, the average thickness of the coating decreases by greater than about fifty percent, greater than about fifty-five percent, greater than about sixty percent, greater than about sixty-five percent, or greater than about ninety percent.

For example, after stent 40 is expanded, the coating can have an average thickness of, e.g., between about 1 μm and about 100 μm, between about 10 μm and 75 μm or between about 25 μm and 60 μm.

Figure 18:
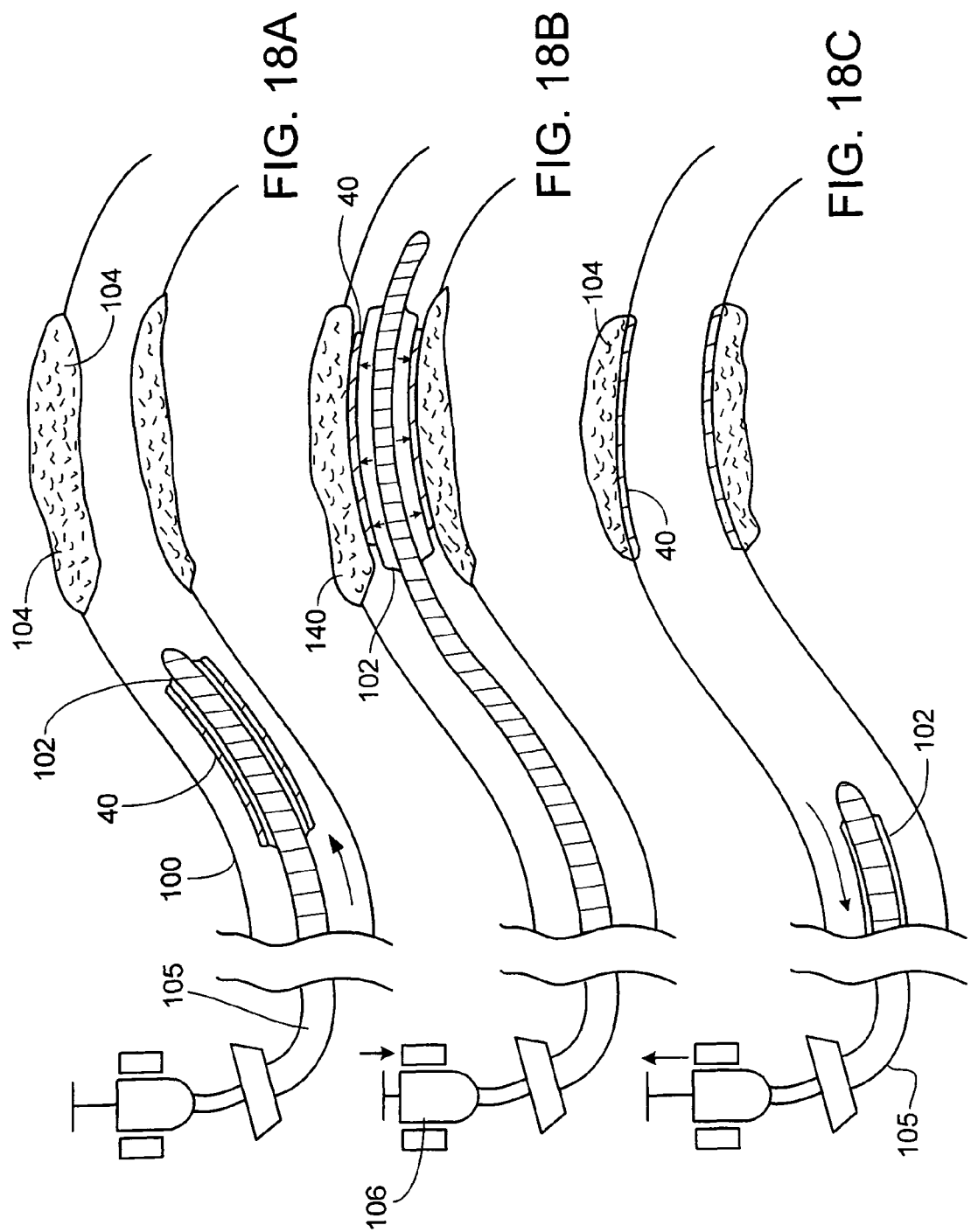
FIGS. 18A-18C illustrate delivery of the stent of FIG. 1 into a body lumen.

To treat a cavity or lumen in a human, e.g., a vascular lumen, e.g., a coronary artery, stent 40 is inserted into a lumen 100, and then expanded within the lumen. Referring particularly to FIGS. 18A and 18B, stent 40 is positioned over an inflatable balloon 102 disposed at a distal end of a delivery catheter 105. Referring particularly to FIGS. 18A, for delivery into the body, the balloon is initially in a small diameter deflated condition and stent 40 is in a small diameter condition over the balloon 102. Referring particularly to FIG. 18B, when the treatment site 104 is reached, the balloon is inflated by actuating the inflation apparatus 106, which provides outward radial force to expand stent 40. Referring particularly to FIG. 18C, after balloon 102 is deflated, the catheter 105 is removed from the body, while the stent 40 remains within lumen 100.

Other Embodiemnts

Other embodiments are within the scope of the claims.

Figure 19:
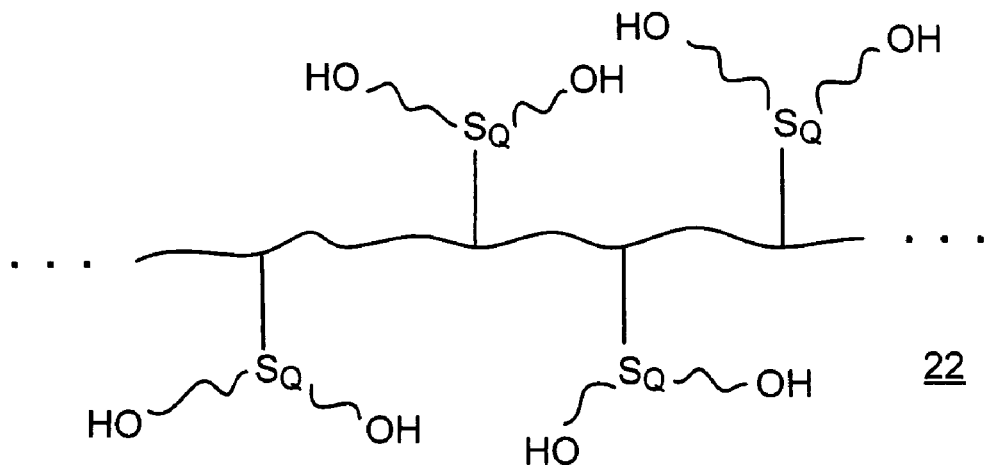
FIG. 19 is a schematic representation of a polymer 22 including a plurality of silsesquioxane units (SQ), each silsesquioxane having two pendent hydroxyl groups.

The silsesquioxanes can be polymer-anchored. Referring to FIG. 19, a polymer 22 includes a plurality of silsesquioxane units (SQ). Each silsesquioxane unit has two pendent hydroxyl groups. Polymer 22 can be reacted with a polyol and an isocyanate to form a polymeric material that can form part of a coating.

Figure 20:
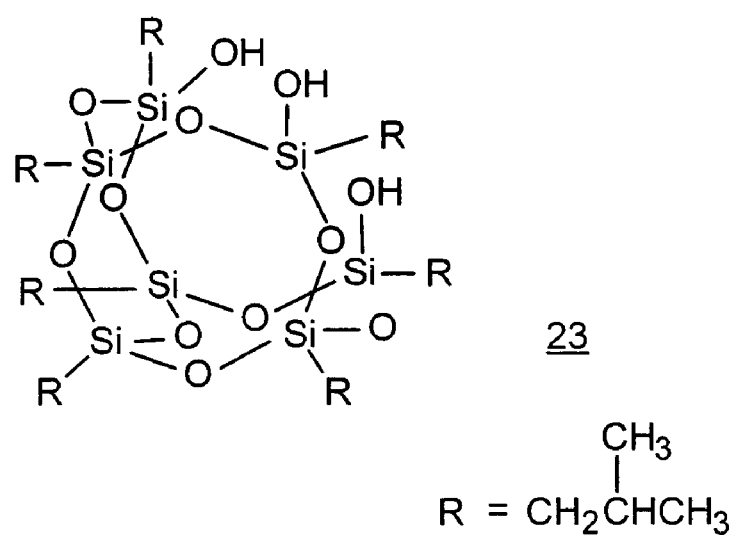
FIG. 20 is a structure of a partially condensed silsesquioxane 1,3,5,7,9,11,14-heptaisobutyltricyclo[7.3.3.1$^{5,11}$]heptasiloxane-endo-3,7,14-triol 23.

Partially condensed silsesquioxanes can be used. For example, 1,3,5,7,9,11,14-heptaisobutyltricyclo[$7.3.3.1^{5,11}$] heptasiloxane-endo-3,7,14-triol 23 of FIG. 20 can be used.

The R substituent of any of the silsesquioxanes described herein can include a C1-C12 primary, secondary, or tertiary alkyl group. Exemplary R groups include methyl, isobutyl, isooctyl, cyclcopentyl, cyclohexyl, phenyl, and the like.

The implantable endoprostheses can have non-circular transverse cross-sections. For example, transverse cross-sections can be polygonal, e.g., square, hexagonal or octagonal.

The metals used to form particular implantable endoprostheses can be degradable in biological systems. Stents made of magnesium or magnesium alloys are examples of such endoprostheses.

The coating can include more than a single layer. For example, the coating can include two layers, three layers or more layers, e.g., five layers.

The implantable endoprostheses can include a tubular member formed from the polymeric material having a drug dispersed within. In addition, the tubular member can include a coating or coatings. The coating or coatings can include a therapeutic agent.

Block copolymers can be used to make the polymeric materials.

The polymeric materials can be configured to be non-degradable in biological systems.

Chiral polyols, isocyanates and/or silsesquioxanes can be used. For example, D-or L-lactide can be used.

The implantable endoprosthesis can be a stent-graft or a covered stent.

The coated endoprosthesis can be configured for non-vascular lumens. For example, it can be configured for use in the esophagus or the prostate. Other lumens include biliary lumens, hepatic lumens, pancreatic lumens, uretheral lumens and ureteral lumens.

The implantable endoprosthesis can be formed from a plastic or plastic alloy, e.g., a degradable plastic or plastic alloy.

Any of the coatings described can also include fillers, e.g., boron nitride, silica, titanium dioxide, montmorillonite, clay, Kevlar®, aluminum nitride, barium and bismuth subcarbonate.

Any of the above coatings can by dyed or rendered radioopaque.

The implantable endoprosthesis can include shapes in memory.

The implantable endoprosthesis can be self-expanding.

The polymeric material can include a reaction product of a polyol and an isocyanate, i.e., not including a silsesquioxane.

What is claimed is:

1. An implantable endoprosthesis comprising a tubular member having a wall defining a lumen inside the wall extending lengthwise through the member and a coating on the wall comprising a polymeric material including a reaction product of a polyol, an isocyanate and a silsesquioxane having at least two pendent hydroxyl groups.

2. The implantable endoprosthesis of claim 1, wherein the coating includes a therapeutic agent.

3. The implantable endoprosthesis of claim 2, wherein the coating includes between about 1 percent by weight and about 35 by weight therapeutic agent.

4. The implantable endoprosthesis of claim 2, wherein the therapeutic agent inhibits restenosis.

5. The implantable endoprosthesis of claim 4, wherein the therapeutic agent that inhibits restenosis comprises paclitaxel.

6. The implantable endoprosthesis of claim 2, wherein the polymeric material fully releases its therapeutic agent in less than seven days in blood at body temperature.

7. The implantable endoprosthesis of claim 1, wherein the polymeric material fully degrades in less than 365 days in blood at body temperature.

8. The implantable endoprosthesis of claim 1, wherein the polyol is selected from the group consisting of be polyethylene glycol, polycaprolactone polyol, polycyclooctene polyol, trans-1,4 butadiene polyol, transisoprene polyol, polynorbornene polyol, polymethacrylate copolymer polyol, polycaprolactone-polylactide copolymer polyol, polycaprolactone-polyglycolide copolymer polyol, polycaprolactone-polylactide-polyglycolide copolymer polyol, polylactide polyol, polycaprolactone-poly($\beta$-hydroxybutyric acid) copolymer polyol, poly($\beta$-hydroxybutyric acid) polyol, and mixtures thereof.

9. The implantable endoprosthesis of claim 1, wherein the polyol has only two pendent hydroxyl groups, and wherein the hydroxyl groups are disposed at ends of the polyol.

10. The implantable endoprosthesis of claim 1, wherein the isocyanate comprises a diisocyanate.

11. The implantable endoprosthesis of claim 10, wherein the diisocyanate is selected from the group consisting of 4,4'-diphenyl methylene diisocyanate, toluene-2,4-diisocyanate, toluene-2,6-diisocyanate, hexamethylene-1,6-diisocyanate, isophorone diisocyanate, and hydrogenated 4,4'-diphenylmethylene diisocyanate, and mixtures thereof.

12. The implantable endoprosthesis of claim 1, wherein the silsesquioxane selected from the group consisting 1-(2-trans-cyclohexanediol)ethyl-3,5,7,9,11,13,15-isobutylpentacyclo-[9.5.1.1$^{3,9}$.1$^{5,15}$.1$^{7,13}$]octasiloxane, 2-ethyl-2-[3-[[(heptaisobutylpentacyclo-[9.5.1.1$^{3,9}$.1$^{5,15}$.1$^{7,13}$]octasiloxanyl)oxy] dimethylsilyl]-propoxy methyl]propane-1,3-diol, 1-(2,3-propanediol)propoxy-3,5,7,9,11,13,15-isobutylpentacyclo-[9.5.1.1$^{3,9}$.1$^{5,15}$.1$^{7,13}$]octasiloxane, 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol, and mixtures thereof.

13. The implantable endoprosthesis of claim 1, wherein a weight ratio of the polyol to the silsesquioxane is from about 1:2 to about 1:30.

14. The implantable endoprosthesis of claim 1, wherein the coating has a thickness of between about 3 micron and about 50 micron before the implantable endoprosthesis is expanded.

15. The implantable endoprosthesis of claim 1, wherein a coverage of the polymeric material on the wall of the tubular member is from about 0.1 µg per square millimeter of surface area of the tubular member to about 10 µg per square millimeter of surface area of the tubular member.

16. The implantable endoprosthesis of claim 1, wherein the wall of the tubular member comprises a material selected from the group consisting of alloys, bioresorbable metals, metal oxides, bioresorbable polymers, and mixtures thereof.

17. The implantable endoprosthesis of claim 1, wherein the polymeric material has an absolute molecular weight of greater than about 50,000.

18. The implantable endoprosthesis of claim 1, wherein the polyol comprises polycaprolactone-polylactide copolymer, and the silsesquioxane comprises 2-ethyl-2-[3-[[(heptaisobutylpentacyclo-[9.5.1.1$^{3,9}$.1$^{5,15}$.1$^{7,13}$]octasiloxanyl)oxy]dimethylsilyl]-propoxy]methyl]-1,3-propanediol.

19. The implantable endoprosthesis of claim 1, wherein the polyol has an absolute molecular weight of from about 5,000 to about 20,000.

20. The implantable endoprosthesis of claim 1, wherein the polymeric material has a glass transition temperature of less than 100° C.

21. The implantable endoprosthesis of claim 1, wherein the polymeric material has a glass transition temperature of within about 10° C. of nominal human body temperature.

22. The implantable endoprosthesis of claim 1, wherein the polymeric material has a storage modulus at 25° C. of less than 1,000 MPa.

23. An implantable endoprosthesis comprising a tubular member that is expandable from a first size to a second size and having a wall defining a lumen inside the wall extending lengthwise through the member and a coating on the wall comprising a polymeric material and a therapeutic agent, wherein during expansion of the implantable endoprosthesis from a first size to a second size, the coating does not substantially crack.

24. The implantable endoprosthesis of claim 23, wherein the polymeric material comprises a reaction product of a polyol, an isocyanate and a silsesquioxane having at least two pendent hydroxyl groups.

25. An implantable endoprosthesis comprising a tubular member having a wall defining a lumen inside the wall extending lengthwise through the member and a coating on the wall comprising a polymeric material and a therapeutic agent, wherein during routine chemical sterilization of the implantable endoprosthesis with ethylene oxide, the coating does not slough off the wall of the tubular member.

26. The implantable endoprosthesis of claim 25, wherein the polymeric material comprises a reaction product of a polyol, an isocyanate and a silsesquioxane having at least two pendent hydroxyl groups.

* * * * *

UNITED STATES PATENT AND TRADEMARK OFFICE
CERTIFICATE OF CORRECTION

PATENT NO.         : 7,976,936 B2
APPLICATION NO.    : 11/111509
DATED              : July 12, 2011
INVENTOR(S)        : Ronald A. Sahatjian et al.

Page 1 of 1

It is certified that error appears in the above-identified patent and that said Letters Patent is hereby corrected as shown below:

Cover Page, under 56, Col. 2, line 1, Other Publications: delete "Themomechanical", and insert -- Thermomechanical --.

Signed and Sealed this
Twentieth Day of September, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,976,936 B2 | Page 1 of 1 |
| APPLICATION NO. | : 11/111509 | |
| DATED | : July 12, 2011 | |
| INVENTOR(S) | : Sahatjian et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1531 days.

Signed and Sealed this
Twenty-second Day of November, 2011

David J. Kappos
*Director of the United States Patent and Trademark Office*